United States Patent
Samain et al.

(10) Patent No.: US 7,521,212 B1
(45) Date of Patent: Apr. 21, 2009

(54) METHOD FOR PRODUCING OLIGOPOLYSACCHARIDES

(75) Inventors: Eric Samain, Gieres (FR); Bernard Priem, Grenoble (FR)

(73) Assignee: Centre National de la Recherche Scientifique (CNRS), Paris (FR)

(*) Notice: Subject to any disclaimer, the term of this patent is extended or adjusted under 35 U.S.C. 154(b) by 264 days.

(21) Appl. No.: 10/019,954

(22) PCT Filed: Jul. 7, 2000

(86) PCT No.: PCT/FR00/01972

§ 371 (c)(1),
(2), (4) Date: May 24, 2002

(87) PCT Pub. No.: WO01/04341

PCT Pub. Date: Jan. 18, 2001

(30) Foreign Application Priority Data

Jul. 7, 1999 (FR) .................................. 99 08772

(51) Int. Cl.
*C12P 19/18* (2006.01)
*C12P 19/26* (2006.01)

(52) U.S. Cl. .................. 435/84; 435/97; 435/193; 536/55.2; 536/55.3; 536/123; 536/123.1; 536/124; 536/126

(58) Field of Classification Search .................. 435/97, 435/193, 440
See application file for complete search history.

(56) References Cited

U.S. PATENT DOCUMENTS 5,945,314 A * 8/1999 Prieto et al. ............... 435/101

FOREIGN PATENT DOCUMENTS

| DE | 197 35 994 | 2/1999 |
| EP | 0 315 496 | 5/1989 |
| EP | 0 392 556 | 10/1990 |
| WO | WO 95 02683 | 1/1995 |
| WO | 96/10086 | * 4/1996 |
| WO | WO 98 44145 | 10/1998 |

OTHER PUBLICATIONS

K.F. Johnson. "Synthesis of Oligosaccharides By Bacterial Enzymes", Glycoconjugated Journal 16(2): 141-146, (Feb. 1999).*
S. Koizumi et al. "Large-Scale Production of UDP-Galactose and Globotriose By Coupling Metqabolically Engineered Bacteria", Nature Biotechnology 16:847-850, (Sep. 1998).*
G.F. Herrmann et al. "Recombinant Whole Cells as Catalysts for the Enzymatic Synthesis of Oligosaccharides and Glycopeptides", Angewandte Chemie International Edition in English 33(12): 1241-1242 (Jun. 6, 1994).*

(Continued)

*Primary Examiner*—Rebecca Prouty
(74) *Attorney, Agent, or Firm*—Foley & Lardner LLP

(57) ABSTRACT

The invention concerns the production by microbiological process of oligopolysaccharides of biological interest. More particularly, the invention concerns a method for synthesizing in vivo oligopolysaccharides by internalization of an exogenous precursor in growing bacterial cells expressing adequate modifying and glycosylating genes.

14 Claims, 9 Drawing Sheets

OTHER PUBLICATIONS

Figure 1:
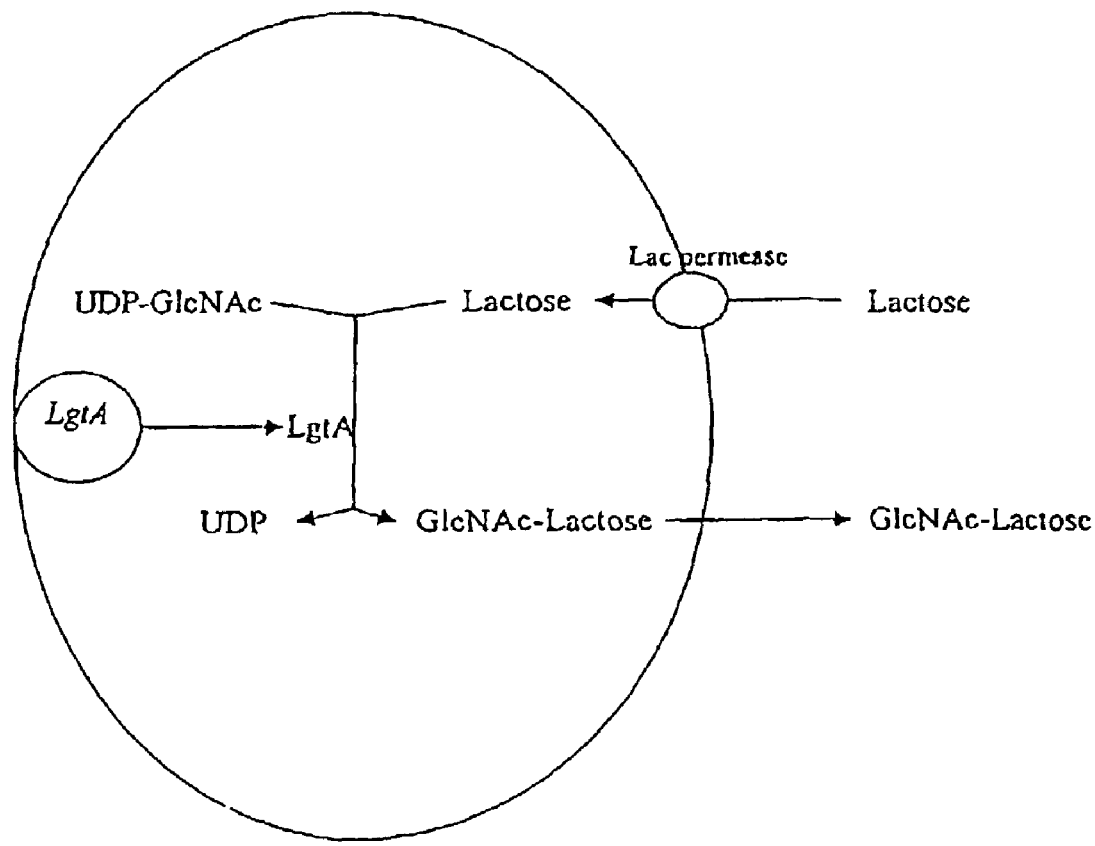

Bettler et al., "The Living Factory: In Vivo Production of N-acetyl-lactosamine containing carbohydrates in *E. coli*", Glycoconjugate Journal, 1999, pp. 205-212, vol. 16, XP002134857, Chapman & Hall., GB.

Samain et al., "Production of O-acetylated and Sulfated Chitooligosaccharides by Recombinant *Escherichia coli* Strains Harboring Different Combinations of Nod Genes", Journal of Biotechnology, 1999, pp. 33-47, vol. 72, No. 1-2, XP004172885, Elsevier Science Publishers, Amsterdam.

Plumbridge et al., "Convergent Pathways for Utilization of the Amino Sugars N-acetylglucosamine, N-acetylmannosamine and N-acetyleneuraminic Acid by *Escherichia coli*", Journal of Bacteriology, 1999, pp. 47-54, vol. 181, No. 1, XP000917021.

* cited by examiner

FIG_5

# METHOD FOR PRODUCING OLIGOPOLYSACCHARIDES

The present invention relates to the or even microbiological production of oligosaccharides of biological interest.

It is now well-established that oligosaccharides play an important biological role especially as regards the activity and function of proteins; thus, they serve to modulate the half-life of proteins, and occasionally they are involved in the structure of the protein. oligosaccharides play an essential role in antigen variability (for example blood groups), and in certain bacterial infections such as those caused by *Neisseria meningitidis*.

As oligosaccharides are usually obtained in a low yield by purification starting from natural sources, the synthesis of oligosaccharides has become a major challenge of carbohydrate chemistry, so as to supply sufficient amounts of well-characterized oligosaccharides, required for fundamental research or for any other potential applications (Boons et al., 1996).

The synthesis of complex oligosaccharides of biological interest may be performed chemically, enzymatically or microbiologically.

Despite the development of new chemical methods for synthesizing oligosaccharides in the course of the last 20 years, the chemical synthesis of oligosaccharides remains very difficult on account of the numerous selective protection and deprotection steps, the lability of the glycoside linkages, the difficulties in obtaining regiospecific couplings, and the low production yields. As the number of steps increases with the size of the oligosaccharide, the preparation of large quantities of oligosaccharides longer than trisaccharides is no simple matter. Contrary to the experience of peptide synthesis or nucleic acid synthesis, traditional synthetic organic chemistry cannot at the present time provide a high-quality and large-quantity synthesis of oligosaccharides, even of simple formula.

Consequently, the enzymatic methods have become more popular since they allow a regioselective synthesis under mild conditions and without a step for protection of the hydroxyl groups. The development of the enzymatic approach was made possible by the cloning and functional identification of numerous genes encoding the enzymes involved in the synthetic pathway of oligosaccharides. Thus, various types of enzyme may be used for the in vitro synthesis of oligosaccharides. The physiological function of the glycosyl-hydrolases and of the glycosyl-phosphorylases is to depolymerize the oligosaccharides, but they may also be used in vitro in the synthesis of oligosaccharides by controlling the reaction equilibrium and kinetics. The substrates of the enzymes for these reactions are readily available, but these enzymatic reactions are not very versatile. Another enzymatic method developed uses the glycosyl-transferases of the Leloir biochemical pathway, which show strong regiospecificity for the precursor and also for the donor substrate; these glycosyl-transferases are not as readily available as the glycosyl-hydrolases. The recombinant DNA technique has recently made it possible to clone and produce a certain number of them. However, the main limitation of this enzymatic method lies in the very high cost of the sugar-nucleotides that are the sugar donors used by these enzymes.

The microbiological route for producing recombinant oligosaccharides in vivo is the most appealing of the synthetic routes since the bacterium is simultaneously responsible for the biosynthesis of the enzymes, the regeneration of the sugar-nucleotides and, finally, the production of the oligosaccharide.

The first descriptions of the microbiological synthesis of oligosaccharides using recombinant bacteria may be considered to a certain extent as the studies which led to the elucidation of the pathways for the biosynthesis of the nodulation factors; these factors are signal molecules secreted by the *rhizobia* to allow recognition by leguminous plants in the nodulation process. Nodulation factors consist of a chito-oligosaccharide backbone bearing various substitutions. The functional identification of the nod genes involved in the biosynthesis of the nodulation factors was partly performed by identifying the oligosaccharides formed in vivo in strains of *Escherichia coli* expressing these various nod genes (Gérémia et al., 1994; Kamst et al., 1995; Spaink et al., 1994; Mergaert et al., 1995). However, the production of oligosaccharides per se was not the aim of these studies; these products were synthesized only in trace amounts and were identified only by means of using radioactive precursors.

On the other hand, it was recently demonstrated in our laboratory (Samain et al., 1997) that the culturing at high cell density of *Escherichia coli* strains containing the nodC (chito-oligosaccharide synthase) gene made it possible to produce large amounts, of greater than 2 g/l, of "recombinant" chito-oligosaccharides.

However, this technique of microbiological synthesis of oligosaccharides remains limited to the production only of chito-oligosaccharides, due to the unique property of nodC (chito-oligosaccharide synthase) of functioning without a precursor; specifically, the other enzymes glycolyze a specific precursor and their activity is thus dependent on the presence of this precursor in the cell. The problem of the precursor is thus the main obstacle blocking the development of the method and its extension to the production of other types of oligosaccharide.

One subject of the present invention is thus a method for producing an oligosaccharide of interest by a genetically modified cell starting with at least one exogenous precursor internalized by said cell, said precursor being involved in the biosynthetic pathway of said oligosaccharide, said method comprising the steps (i) of obtaining a cell that comprises at least one recombinant gene encoding an enzyme capable of modifying said exogenous precursor or one of the intermediates in the biosynthetic pathway of said oligosaccharide from said exogenous precursor necessary for the synthesis of said oligosacchariden from said precursor, and also the components for expressing said gene in said cell, said cell lacking any enzymatic activity liable to degrade said oligosaccharide, said precursor and said intermediates; (ii) of culturing said cell in the presence of at least one said exogenous precursor, under conditions enabling the internalization according to a mechanism of passive and/or active transport of said exogenous precursor by said cell and the production of said oligosaccharide by said cell.

According to one particular embodiment, the present invention relates to a method as described above, characterized in that said cell also comprises at least one gene encoding an enzyme capable of modifying an endogenous precursor involved in the biosynthetic pathway of said oligosaccharide, said enzyme being identical to or different than the enzyme used in the method described above, and also to the components for expressing said gene in said cell and characterized in that said cell lacks any enzymatic activity liable to degrade said precursor.

The term "oligosaccharides" is intended to denote linear or branched polymers with a variable number of residues, linkages and subunits; the number of residues being greater than 1. Oligosaccharides are carbohydrates that become converted on hydrolysis into several monosaccharide molecules; the monosaccharides being sugars that cannot be converted into a simpler substance by hydrolysis. Monosaccharides are subdivided into trioses, tetroses, pentoses, hexoses and heptoses depending on the number of carbon atoms in their hydrocarbon-based chain, and also into aldoses and ketoses depending on the presence of an aldehyde function or a ketone function in their molecule. Among the monosaccharides that are most frequently encountered, mention may be made of mannose, glucose, galactose, N-acetylglucosamine and N-acetylgalactosamine. The number of chains of stereoisomeric oligosaccharides is extremely large, due to the large number of asymmetric carbons in the hydrocarbon-based chain.

The expression "exogenous precursor" is intended to denote a compound involved in the biosynthetic pathway of the oligosaccharide according to the invention that is internalized by said cell. The expression "endogenous precursor" is intended to denote a compound involved in the biosynthetic pathway of the oligosaccharide according to the invention that is naturally present in said cell.

The expression "genetically modified cell" is intended to denote a microorganism in which at least one alteration of the DNA sequence has been introduced into its genome in order to give said cell a particular phenotype. Such alterations may thus, for example, give the cell the ability not to degrade or not to modify a compound according to the invention, or not to reduce the DNA rearrangement frequency.

The method according to the invention is characterized in that said cell is a cell chosen from bacteria and yeasts. According to one preferred embodiment of the invention, the bacterium is chosen from the group composed of *Escherichia coli, Bacillus subtilis, Campylobacter pylori, Helicobacter pylori, Agrobacterium tumefaciens, Staphylococcus aureus, Thermophilus aquaticus, Azorhizobium caulinodans, Rhizobium leguminosarum, Neisseria gonorrhoeae* and *Neisseria meningitis*. According to one preferred embodiment of the invention, the bacterium is *Escherichia coli*. According to another embodiment of the invention, the cell is a yeast that is preferably *Saccharomyces cerevsae, Saccharomyces pombe* or *Candida albicans*. The cell according to the invention lacks any enzymatic activity liable to degrade said oligosaccharide, said precursor or said metabolic intermediates.

The nucleic acid sequence encoding the enzyme according to the invention is either naturally present in said cell or is introduced into said cell by the recombinant DNA techniques known to those skilled in the art. In the present description, the term "nucleic acid" will be intended to denote a DNA fragment, which is either double-stranded or single-stranded, or products of transcription of said DNAs, and/or an RNA fragment. According to one preferred embodiment, the nucleic acid sequence which is introduced into said cell by the recombinant DNA techniques and which encode an enzyme involved in the biosynthetic pathway of the oligosaccharide of interest is heterologous. The expression "heterologous nucleic acid sequence" is intended to denote a nucleic acid sequence that is not naturally present in the cell according to the invention. The heterologous nucleic acid sequence according to the invention may originate from any animal or plant, eukaryotic or prokaryotic cell type and may originate from viruses.

Among the prokaryotic cells from which the heterologous nucleic acid sequence originates, mention should be made of bacteria and in particular *Escherichia coli, Bacillus subtilis, Campylobacter pylori, Helicobacter pylori, Agrobacterium tumefaciens, Staphylococcus aureus, Thermophilus aquaticus, Azorhizobium caulinodans, Rhizobium leguminosarum, Rhizobium meliloti, Neisseria gonorrhoeae* and *Neisseria meningitis*.

Among the unicellular eukaryotic cells from which the heterologous nucleic acid sequence originates, mention should be made of yeasts and in particular *Saccharomyces cerevisae, Saccharomyces pombe* and *Candida albicans*.

According to one preferred embodiment, the heterologous nucleic acid sequence originates from plant or animal eukaryotic cells. According to an even more preferred embodiment, the heterologous nucleic acid sequence originates from mammalian cells and preferably from human cells.

According to one preferred embodiment of the invention, the cell according to the invention is the bacterium *Escherichia coli* and the nucleic acid sequence introduced into the bacterium and encoding the enzyme according to the invention preferably originates from a bacterium chosen from the group mentioned above.

According to one preferred embodiment of the invention, the nucleic acid sequence encoding the enzyme according to the invention is introduced into said cell in the form of an expression vector. The vector must comprise a promoter, translation start and stop signals, and also regions suitable for regulating transcription. The vector must be able to be maintained stably in the cell over successive generations and can optionally contain particular signals specifying the secretion of the translated enzyme. These various control signals are chosen as a function of the host cell used. To this end, the nucleic acid sequences may be inserted into autonomous replication vectors within the chosen host or into integrative vectors which become integrated into the genome of the chosen host. Such vectors are prepared according to the methods commonly used by those skilled in the art, and the clones resulting therefrom may be introduced into a suitable host cell by standard methods such as, for example, heat shock or electroporation.

The invention is also directed toward the above cells, characterized in that they are transformed by at least one recombinant isolated nucleic acid encoding the enzyme according to the invention or by at least one recombinant vector as defined above.

The method according to the invention is characterized in that said modification made by said enzyme is chosen from glycosylation, sulfatation, acetylation, phosphorylation, succinylation, methylation and addition of an enolpyruvate group, sialylation and fucosylation. More particularly, the method according to the invention is characterized in that said enzyme is an enzyme capable of carrying out a glycosylation, which is chosen from glycosyl-transferases, glycosyl-hydrolases and glycosyl-phosphorylases. According to one preferred embodiment, the enzyme capable of carrying out the glycosylation is a glycosyl-transferase. According to one preferred embodiment, the glycosyl-transferase according to the invention is chosen from β-1,3-N-acetyl-glucosaminyl-transferase, β-1,3-galactosyl-transferase, α-1,3-N-acetyl-galactosaminyl-transferase, β-1,3-glucuronosyl-transferase, β-1,3-N-acetyl-galactosaminyl-transferase, β-1,4-N-acetyl-galactosaminyl-transferase, β-1,4-galactosyl-transferase, α-1,3-galactosyl-transferase, α-1,4-galactosyl-transferase, α-2,3-sialyl-transferase, α-2,6-sialyl-transferase, α-2,8-sialyl-transferase, α-1,3-fucosyl-transferase, α-1,4-fucosyl-transferase and α-1,2-fucosyl-transferase. The glycosyl-transferases used in the present invention are capable of stereospecific conjugation of specific activated saccharide units on a specific acceptor molecule. The activated saccharides generally consist of uridine diphosphate, guanosine diphosphate and cytidine diphosphate saccharide derivatives. Thus, the activated saccharides may be a UDP-saccharide, a GDP-saccharide or a CMP-saccharide.

Certain genes encoding glycosyl-transferases used in the method according to the invention have been described previously; thus, international patent application WO 96/10086 describes the standard oligosaccharide synthesis: in a first step, the various glycosyl-transferases are produced in recombinant bacteria containing the lgtA, lgtB and lgtC genes of *Neisseria gonorrhoeae*, and, after purifying the recombinant enzymes thus produced, the oligosaccharides are synthesized in vitro in the presence of the required precursors and sugar-nucleotides.

According to certain embodiments of the invention, the enzyme capable of performing an acetylation is encoded by the NodL gene of the bacterium *Azorhizobium caulinodans*. According to another embodiment, the enzyme capable of performing a sulfatation is encoded by the NodH gene of the bacterium *Rhizobium meliloti*.

The method according to the invention is characterized in that said cell culturing is preferably performed on a carbon-based substrate; according to one particular embodiment of the invention, said carbon-based substrate is chosen from glycerol and glucose. Other carbon-based substrates may also be used; mention should be made of maltose, starch, cellulose, pectin and chitin. According to another embodiment, the cell culturing is performed on a substrate composed of amino acids and/or protein and/or lipids.

The method according to the invention is characterized in that said culturing step is performed under conditions allowing the production of a culture with a high cell density; this culturing step comprises a first phase of exponential cell growth ensured by said carbon-based substrate, a second phase of cell growth limited by said carbon-based substrate which is added continuously, and finally a third phase of slowed cell growth obtained by continuously adding to the culture an amount of said substrate that is less than the amount of substrate added in step b) so as to increase the content of oligosaccharides produced in the high cell density culture.

The method according to the invention is characterized in that the amount of substrate added continuously to the cell culture during said phase c) is at least 30% less, preferentially 50% and preferably 60% less than the amount of substrate added continuously during said phase b). The method according to the invention is also characterized in that said exogenous precursor is added during phase b).

According to one embodiment of the invention, the method is characterized in that said exogenous precursor is of carbohydrate nature, preferably of oligosaccharide nature.

The novelty and feasibility of the method according to the invention is based on the use of two modes of internalization of the exogenous precursor that do not destroy the integrity of the cell or attack its vital functions. This especially excludes the standard techniques of membrane permeabilization with organic solvents which block growth and energy metabolism. The two possible modes for internalizing the exogenous precursor use a passive or active transport mechanism.

The invention relates firstly to a method that is characterized in that said exogenous precursor is internalized according to a passive transport mechanism. The expression "internalization by passive transport" is intended to denote the passive diffusion of any of the exogenous precursor across the plasma membrane, the molecular flow being oriented from the zones of highest concentration to the zones of lowest concentration so as to tend finally toward a state of equilibrium. The internalization by passive transport consists in using an exogenous precursor that is small enough and hydrophobic enough to diffuse passively across the membrane. A monosaccharide precursor whose anomeric position is blocked with an alkyl substitute constitutes an example of a precursor that may be internalized in this manner. The present invention thus relates to a method that is characterized in that said exogenous precursor is a monosaccharide whose anomeric carbon is linked to an alkyl group; preferably, said alkyl group is an allyl group. One of the objects of the invention is thus to provide a method for producing oligosaccharides that contain a functionalizable group such as the allyl group and that can consequently be used as precursors for the chemical synthesis of glycoconjugates (neoglycoprotein or neoglycolipids) or glycopolymers. The reason for this is that the double bond of the allyl group is able to be opened by ozonolysis to form an aldehyde and to allow the oligosaccharide to conjugate onto a protein by reductive amination (Roy et al., 1997). Another route is the addition of cysteamine (Lee and Lee, 1974, Roy et al., 1997) to the allylic double bond to form an amine end group which may react, for example, with the carboxylic groups of proteins.

According to one particular embodiment, the method according to the invention concerns the production of (β-D-Gal-[1→4]-β-D-GlcNac-1→O-allyl); the method is characterized in that said cell is a bacterium of LacZ⁻ genotype, said enzyme is β-1,4-galactosyl-transferase, said substrate is glycerol and said precursor is allyl-N-acetyl-β-D-glucosaminide (β-D-GlcNac-1→O-allyl). Finally, according to another particular embodiment, the method according to the invention is characterized in that the double bond of the allyl group of said (β-D-Gal-[1→4]-β-D-GlcNac-1→O-allyl) is chemically modified by addition, oxidation or ozonolysis reactions.

The present invention also relates to a method that is characterized in that said precursor is internalized according to an active transport mechanism. The expression "internalization by active transport" is intended to denote the ability of cells and preferably of bacteria to selectively admit and concentrate certain exogenous substances or precursors into their cytoplasm. This transport is performed by transporters of protein nature known as permeases, which act as enzymes; permeases are inducible catalysts, that is to say catalysts that are synthesized in the presence of the substrate or the precursor. According to one particular embodiment of the invention, lactose and β-galactosides constitute precursors that are actively transported into the cytoplasm of the bacterium *Escherichia coli* by lactose permease, also known as galactoside permease. The invention thus relates to a method according to the invention that is characterized in that said active transport of said precursor is performed by lactose permease. Lactose permease has fairly broad specificity, which allows it to transport molecules other than lactose.

The reason for this is that it is capable of transporting various natural or synthetic β-galactosides, α-galactosides and sucrose. One of the objects of the invention is thus to provide, according to a preferred embodiment, a method that is characterized in that said precursor is lactose, which constitutes the base moiety for a great many biologically active oligosaccharides. It is also within the scope of the invention to provide a method that is characterized in that said precursor is chosen from the group composed of: (i) natural or synthetic β-galactosides, preferably from 4-O-β-D-galactopyranosyl-D-fructofuranose (lactulose), 3-O-β-D-galactopyranosyl-D-arabinose and allyl-β-D-galactopyranoside, (ii) α-galactosides, preferably melibiose and raffinose, and allyl-α-D-galactopyranoside, (iii) sucrose.

The specificity of lactose permease may even be modified by mutation and allow the transport of other compounds such as maltose and cellobiose. All these compounds may thus be used as precursors for the synthesis of oligosaccharides. It is also within the scope of the invention to use as precursors lactose analogs containing a chemically reactive group for a subsequent functionalization of the product; preferably, one of these analogs is allyl-β-D-galactopyranoside. It is also within the scope of this invention to use other permeases possibly modified by recombinant DNA techniques to allow the internalization of different types of precursor.

The β-galactosides are normally hydrolyzed in the cytoplasm of the bacterium by the β-galactosidase encoded by the LacZ gene. In order to overcome this problem, a lacZ$^-$ bacterial mutant lacking β-galactosidase activity is used when the precursor used is lactose and/or a β-galactoside. One of the objects of the invention is thus also to provide the method according to the invention that is characterized in that said cell lacks enzymatic activity liable to degrade said precursor or said metabolic intermediates.

According to one particular embodiment, the invention relates to a method described above that is characterized in that said precursor is sialic acid. In this case, said active transport of said precursor is performed by NanT permease.

According to another particular embodiment, the invention relates to a method described above that is characterized in that said precursor is sialic acid and lactose. In this case, said active transport of said precursor is performed by lactose permease and NanT permease.

In the method according to the invention, said cell may be lacking in enzymatic activity liable to degrade said precursor(s).

According to one preferred embodiment, the method is characterized in that said cell has a genotype chosen from LacZ$^-$ and/or NanA$^-$.

According to another aspect of the invention, the method is characterized in that it also comprises the addition of an inducer to said culture medium to induce the expression in said cell of said enzyme and/or of a protein involved in said active transport; according to one preferred embodiment, the method according to the invention is characterized in that said inducer is isopropyl β-D-thiogalactoside (IPTG) and said protein is lactose permease.

The invention makes it possible for the first time to produce complex oligosaccharides in yields of the order of one gram per liter. Depending on its size, the oligosaccharide either accumulates in the bacterial cytoplasm or is secreted into the culture medium. Thus, according to one preferred embodiment, the method according to the invention is used for the production of the trisaccharide 4-O-[3-O-(2-acetamido-2-deoxy-β-D-glucopyranosyl)-β-D-galactopyranosyl]-D-glucopyranose, (β-D-GlcNac-[1→3]-β-D-Gal-[1→4]-D-Glc); it is characterized in that said cell is a bacterium of LacZ$^-$, LacY$^+$ genotype, said enzyme is β-1,3-N-acetyl-glucosaminyl-transferase, said substrate is glycerol, said inducer is isopropyl β-D-thiogalactoside (IPTG) and said precursor is lactose.

According to a second preferred embodiment, the method according to the invention is used for the production of lacto-N-neo-tetraose and polylactosamine; it is characterized in that said cell is a bacterium of LacZ$^-$, LacY$^+$ genotype, said enzymes are β-1,3-N-acetyl-glucosaminyl-transferase and β-1,4-galactosyl-transferase, said substrate is glucose, said inducer is isopropyl-β-D-thiogalactoside (IPTG) and said precursor is lactose.

According to a third preferred embodiment, the method according to the invention is used for the production of allyl 3-O-(2-acetamido-2-deoxy-β-D-glucopyranosyl)-β-D-galactopyranoside, (β-D-GlcNac-[1→3]-β-D-Gal-1→O-allyl); it is characterized in that said cell is a bacterium of LacZ$^-$, LacY$^+$ genotype, said enzyme is β-1,3-N-acetyl-glucosaminyl-transferase, said substrate is glycerol, said inducer is isopropyl β-D-thiogalactoside (IPTG) and said precursor is allyl-β-D-galactopyranoside.

According to a fourth preferred embodiment, the method according to the invention is used for the production of analogs of lacto-N-neo-tetraose and of polylactosamines in which the glucose residue is replaced with an allyl group; it is characterized in that said cell is a bacterium of LacZ$^-$, LacY$^+$ genotype, said enzymes are β-1,3-N-acetyl-glucosaminyl-transferase and β-1,4-galactosyl-transferase, said substrate is glucose, said inducer is isopropyl β-D-thiogalactoside (IPTG) and said precursor is allyl-β-D-galactopyranoside.

According to a fifth preferred embodiment, the method according to the invention is used for the production of allyl-β-D-lactosamine (β-D-Gal-[1→4]β-D-GlcNac-1→O-allyl); it is characterized in that said cell is a bacterium of LacZ$^-$, LacY$^+$ genotype, said enzyme is β-1,4-galactosyl-transferase, said substrate is glycerol and said precursor is allyl-N-acetyl β-D-glucosaminide (β-D-GlcNac-[1→O-allyl]).

The invention also relates to a method that makes it possible to envisage the production of a large number of different oligosaccharides obtained by glycosylation of lactose. Specifically, besides the genes lgtA and lgtB which respectively encode β-1,3-N-acetyl-glucosaminyl-transferase and β-1,4-galactosyl-transferase, several genes of bacterial glycosyl-transferases using lactose as precursor have recently been cloned. These are lgtC (β-1,4-galactosyl-transferase) and Lst (α-2,3-sialyl-transferase) (Gilbert et al., 1997). Using these genes in a method according to the invention makes it possible to produce molecules such as globotriose (p$^k$ blood antigen) and sialyl-lactose. Moreover coexpression of the lgtA and lgtB genes with the gene for α-1,3-fucosyl-transferase from *Helicobacter pylori* (Martin et al., 1997) according to a method according to the invention makes it possible to obtain Lewis$^x$ pentasaccharide. The addition of the Lst (α-2,3-sialyl-transferase) gene gives access to the sialyl Lewis$^x$ hexasaccharide.

The method according to the invention also makes it possible to obtain a large number of different oligosaccharides obtained by glycosylation of exogenous precursors other than lactose and transported by lactose permease or by other permeases.

The method according to the invention makes it possible to obtain a large number of different oligosaccharides obtained by in vivo modification (sulfatation, acetylation, phosphorylation, succinylation, methylation, addition of an enolpyruvate group) of precursors. The synthesis of certain oligosaccharides may necessitate the modification of endogenous precursors, in addition to the modification of exogenous precursors. Thus, it may be envisaged to introduce into a K12 *Escherichia coli* bacterium the gene for the enzyme involved in the metabolism of an endogenous precursor to allow the production of certain sugar-nucleotides such as, for example, CMP-sialic acid, UDP-GalNAc or GDP-fucose, which are not normally produced by this bacterial strain, so as to achieve the synthesis of an oligosaccharide of interest. For example, UDP-GalNAc may be produced from UDP-GlcNAc if the epimerase gene is introduced into a cell according to the invention.

Contrary to the enzymatic method for the in vitro synthesis of oligosaccharides, which requires the use of very expensive molecules such as ATP, acetyl-CoA, PAPS (adenosine 3'-phosphate 5'-phosphosulfate) or phospho-enolpyruvate, one of the advantages of the present invention lies in the fact that these molecules are naturally recycled into the cell, thus making it possible to reduce the production costs of the oligosaccharides.

Another subject of the invention relates to a method described above for the production of 3'-sialyllactose (α-NeuAc-[2→3]-→-D-Gal-[1→4]-β-D-Glc) or 6'-sialyllactose (α-NeuAc-[2→6]-β-D-Gal-[1→4]-β-D-Glc), characterized in that:
- said cell is a bacterium of LacZ⁻, LacY⁺, NanA⁻ or NanT⁺ genotype;
- said enzymes are CMP-NeuAc-synthase and α-2,3-sialyl-transferase or α-2,6-sialyl-transferase;
- said substrate is glycerol;
- said inducer is isopropyl-β-D-thiogalactoside (IPTG);
- said precursors are lactose and sialic acid.

According to a sixth preferred embodiment which completes the second embodiment described above, the method according to the invention is. used for the production of a sialyl derivative of lacto-N-neo-tetraose and of polylactosamine (lacto-N-neo-hexaose, lacto-N-neo-octaose, lacto-N-neo-decaose), characterized in that it also comprises a said enzyme chosen from α-2,3-sialyl-transferase and α-2,6-sialyl-transferase, and in that said cell also has a NanA⁻, NanT⁺ genotype and expresses the CMP-NeuAc-synthase gene, said acceptors are lactose and sialic acid.

Another subject of the invention relates to a method described above for the production of lacto-N-neo-tetraose, β-D-Gal[1→4]-β-D-GlcNAc[1→3]-β-D-Gal[1→4]-(α-L-Fuc-[1→3])-β-D-Glc, β-D-Gal[1→4]-(α-L-Fuc-[1→3])-β-D-GlcNAc[1→3]-β-D-Gal [1→4]-(α-L-Fuc-[1→3])-β-D-Glc, β-D-Gal[1→4]-(α-L-Fuc-[1→3])-β-D-GlcNAc [1→3]-D-Gal [1-4]-β-D-GlcNAc-[143]-β-D-Gal[1→4]-(α-L-Fuc-[1→3])-β-D-Glc, characterized in that
- said cell is a bacterium of LacZ⁻, LacY⁺, WcaJ⁻ genotype and overexpresses rcsA;
- said enzymes are β-1,3-N-acetyl-glucosaminyl-transferase, β-1,4-galactosyl-transferase and α-1,3-fucosyl-transferase;
- said substrate is glucose;
- said inducer is isopropyl-β-D-thiogalactoside (IPTG);
- said precursor is lactose.

According to a seventh preferred embodiment, the method according to the invention is used for the production of 3'-fucosyllactose (β-D-Gal-[1→4]-(α-L-Fuc-[1→3]-D-Glc) or 2'-fucosyllactose (β-D-Gal-[1→2]-(α-L-Fuc-[1→3]-D-Glc), characterized in that it comprises a said enzyme chosen from α-1,3-fucosyl-transferase or α-1,2-fucosyl-transferase, and in that the cell has a wcaj⁻ lacZ⁻ genotype and overexpresses the rcsA gene and in that said precursor is lactose.

According to an eighth preferred embodiment, the method according to the invention is used for the production of a fucosyl derivative of lacto-N-neo-tetraose and of polylactosamine (lacto-N-neo-hexaose, lacto-N-neo-octaose, lacto-N-neo-decaose), characterized in that it also comprises a said enzyme chosen from α-1,2-fucosyl-transferase and α-1,3-fucosyl-transferase, and in that said cell also has a WcaJ⁻ genotype and overexpresses the RcsA gene, said acceptor being lactose.

According to a ninth preferred embodiment, the method according to the invention is used for the production of a sialyl and fucosyl derivative of lacto-N-neo-tetraose, lacto-N-neo-decaose), characterized in that it also comprises a said enzyme chosen from α-2,3-sialyl-transferase and α-2,6-sialyl-transferase, and also a said enzyme chosen from α-1,2-fucosyl-transferase and α-1,3-fucosyl-transferase, and in that said cell also has a NanA⁻, NanT⁺, WcaJ⁻ genotype and overexpresses the RcsA gene and the gene for CMP-NeuAc-synthase, said acceptors are lactose and sialic acid.

The methods of embodiments 1 to 9 mentioned above may be carried out for the production of oligosaccharide analogs in which the glucose residue is replaced with an allyl group, said precursor now being allyl-β-D-galactoside rather than lactose.

Another object of the invention is to provide a method for producing oligosaccharides that are labeled with or enriched in radioisotopes; such oligosaccharides are extremely precious for fundamental biological or conformational analysis studies. The invention thus relates to a method for producing an oligosaccharide that is labeled with at least one radioisotope, characterized in that said cell is cultured on said carbon-based substrate labeled with said radioisotope and/or in the presence of a said precursor labeled with said radioisotope. The radioisotopes are preferably chosen from the group composed of: $^{14}C$, $^{13}C$, $^{3}H$, $^{35}S$, $^{32}P$, $^{33}P$.

The invention also relates to an oligosaccharide which may be obtained by a method according to the invention.

According to one particular embodiment, the invention relates to an activated oligosaccharide that may be used for the chemical synthesis of glycoconjugates or glycopolymers that may be obtained by a method as described above, said oligosaccharide being characterized in that the double bond of the allyl group is chemically modified by addition, oxidation or ozonolysis reactions.

The oligosaccharide according to the invention is useful in a wide range of therapeutic and diagnostic applications; it may be used, for example, as an agent for blocking cell surface receptors in the treatment of a host of diseases involving cellular adhesion, or may be used as nutritional supplements, antibacterial agents, anti-metastatic agents and anti-inflammatory agents. The invention thus relates to an oligosaccharide according to the invention as a medicinal product, and especially as a medicinal product intended for selectively preventing the adhesion of biological molecules. The oligosaccharide according to the invention is also used as a medicinal product intended for treating cancer, inflammation, heart diseases, diabetes, bacterial infections, viral infections and neurological diseases and as a medicinal product intended for grafts. The invention also relates to a pharmaceutical composition, characterized in that it comprises an oligosaccharide according to the invention and a pharmaceutically acceptable vehicle.

Finally, the invention also relates to the agricultural and agronomic use of an oligosaccharide according to the invention, especially for the growth and defense of plants. Specifically, oligosaccharides play a predominant role in *Rhizobium*/leguminous plant symbiosis. Indeed, certain oligosaccharides originating from the hydrolysis of fungal or plant glycoproteins or walls can act as plant hormones or as elicitors of defense reactions in plants.

The industrial advantage of the method according to the invention is obvious since it makes it possible for the first time to achieve a production of the order of a kilogram of complex oligosaccharides of biological interest. All the oligosaccharides of biological interest that we envisage synthesizing at the industrial scale are currently available only at the mg scale and at extremely high costs (up to 1 million FFr per gram); the cost price of these compounds produced by the present microbiological route are infinitely lower.

The characteristics and advantages of the present invention will be demonstrated more clearly on reading the examples and figures which follow, the keys to which are represented below.

FIGURES

FIG. 1: Principle of the method for producing the trisaccharide 4-O-[3-O-(2-acetamido-2-deoxy-β-D-gluco-pyranosyl)-β-D-galactopyranosyl]-D-glucopyranose, (β-D-GlcNAc-[1→3]-β-D-Gal-[1→4]-D-Glc)

Lactose (β-D-Gal-[1-4]-β-D-Glc) is transported into the cell by lactose permease (Lac permease). The lactose cannot be hydrolyzed in the cell since the strain is a LacZ⁻ mutant. Expression of the lgtA gene allows the production of the LgtA enzyme which transfers a GlcNAc from UDP-GlcNAc onto a lactose molecule. The trisaccharide formed (β-D-GlcNAc-[1-3]-β-D-Gal-[1-4]-D-Glc) is excreted into the medium.

Figure 2:
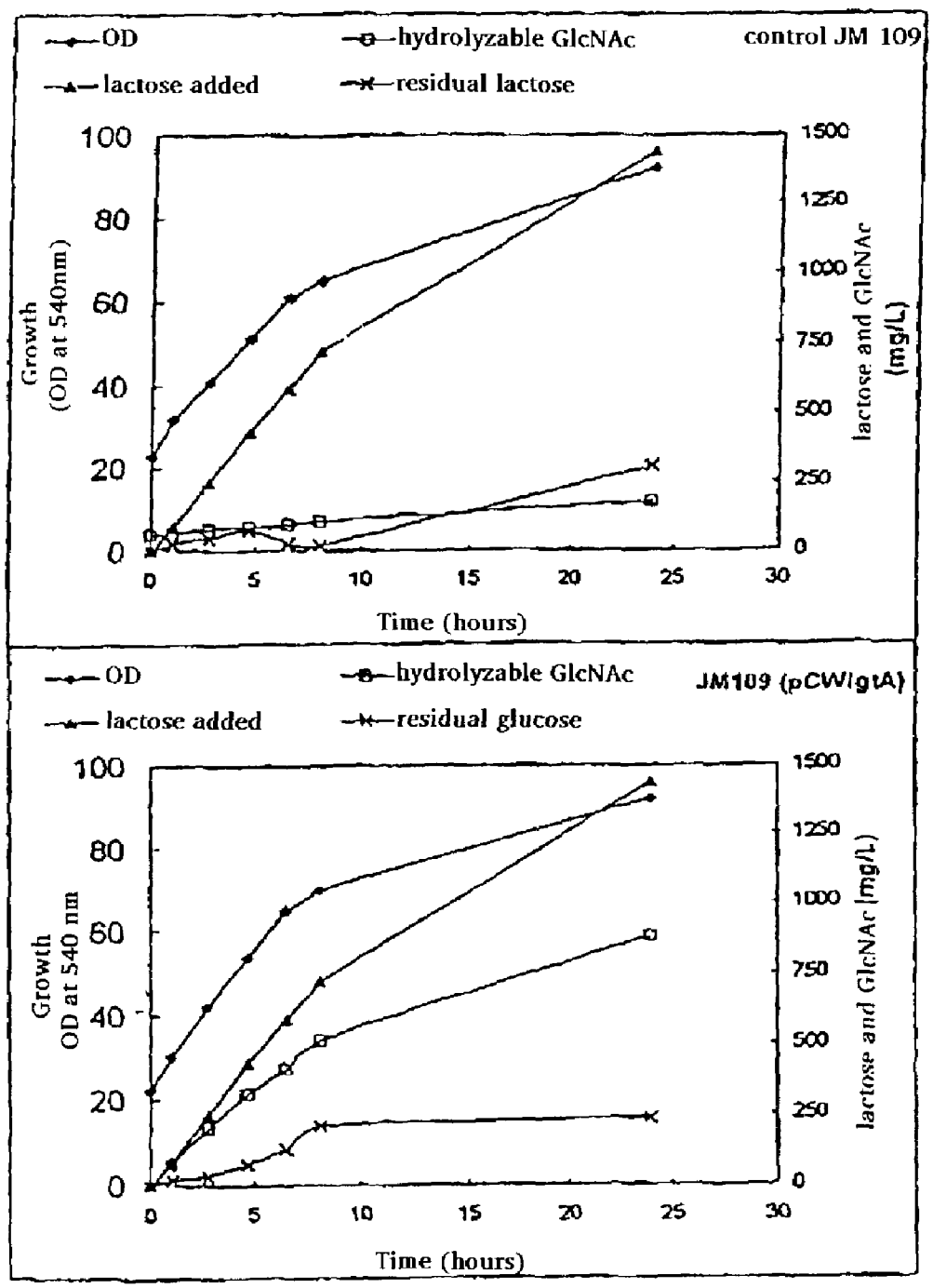

FIG. 2: High cell density culturing of the control strain JM 109 and of the strain JM 109 (pCWlgtA) containing the glycosyl transferase gene LgtA Lactose is added continuously and the residual lactose is determined enzymatically. The concentration of hydrolyzable GlcNAc in the culture medium is measured calorimetrically after acid hydrolysis. The added lactose represents the total cumulative amount of lactose which was added continuously.

Figure 3:
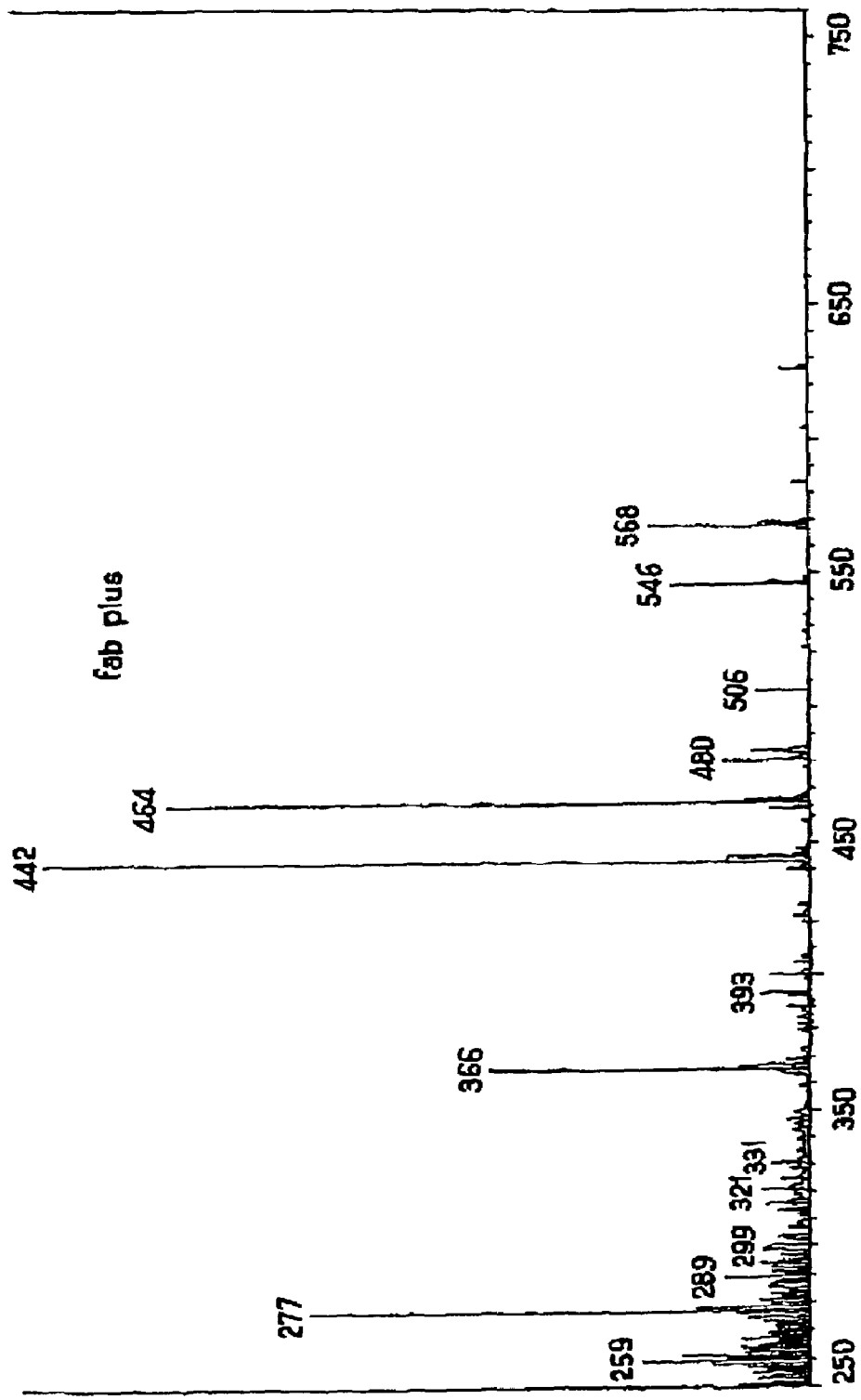

FIG. 3: Mass spectrum in FAB⁺ mode of the trisaccharide 4-O-[3-O-(2-acetamido-2-deoxy-β-D-gluco-pyranosyl)-β-D-galactopyranosyl]-D-glucopyranose, (β-D-GlcNAc-[1→3]-β-D-Gal-[1→4]-D-Glc) purified from the culture supernatant of the strain JM 109 (lgtA)

The two quasi-molecular ions [M+H]⁺ and [M+Na]⁺ are observed at m/z 546 and 568. An ion [M+H]⁺ at m/z 442 is also observed, which is due to the presence of β-D-GlcNAc-[1-3]-IPTG. This indicates that the IPTG (isopropyl β-D-thiogalactose) used to induce Lac permease and LgtA is also glycosylated.

Figure 4:
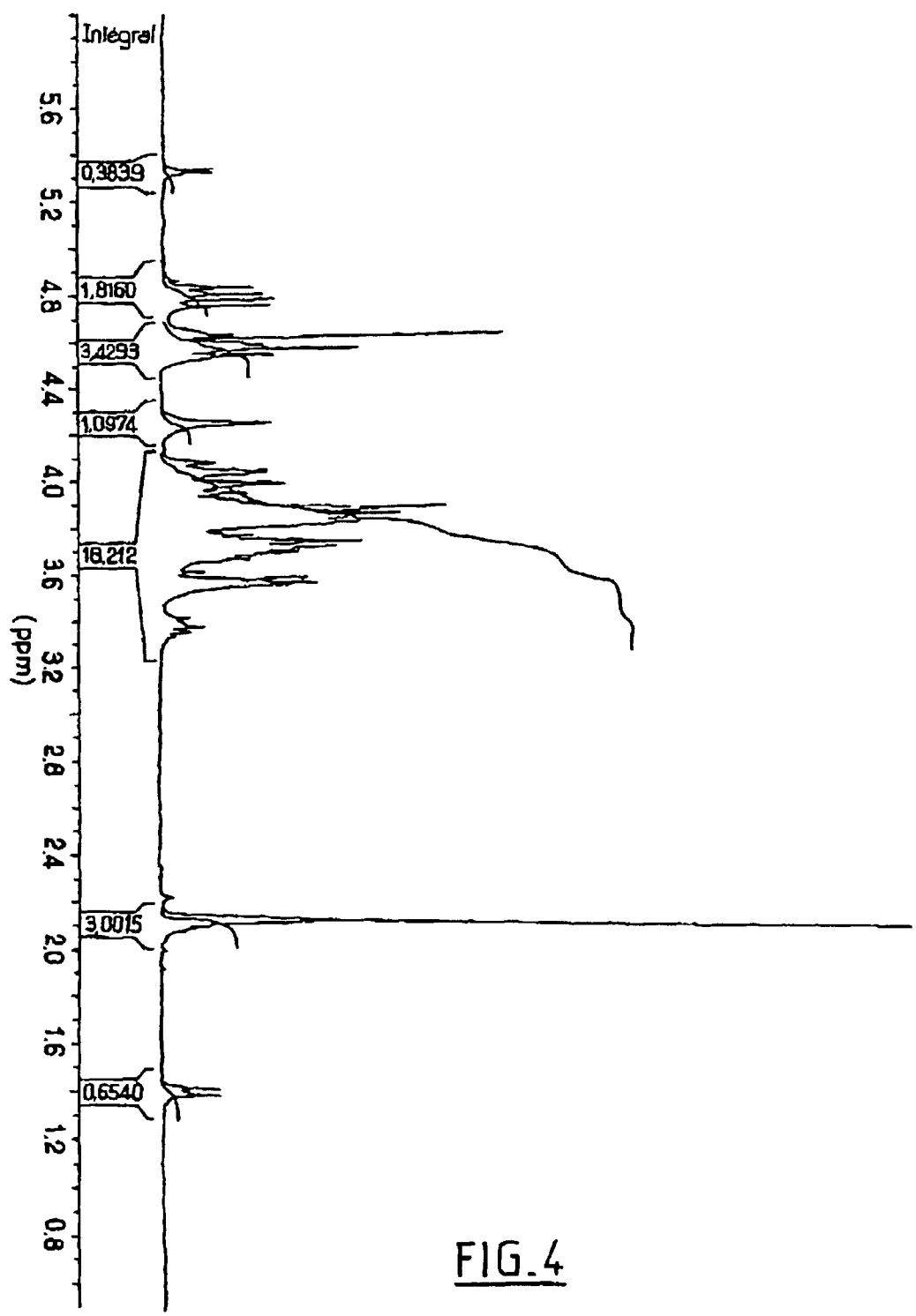

FIG. 4: Proton NMR spectrum of the trisaccharide 4-O-[3-O-(2-acetamido-2-deoxy-β-D-glucopyranosyl)-β-D-galactopyranosyl]-D-glucopyranose, (β-D-GlcNAc-[1→3-]1-β-D-Gal-[1→4]-D-Glc) at 323° K The signal at 1.4 ppm is due to the protons of the isopropyl group of the glycosylated IPTG derivative.

Figure 5:
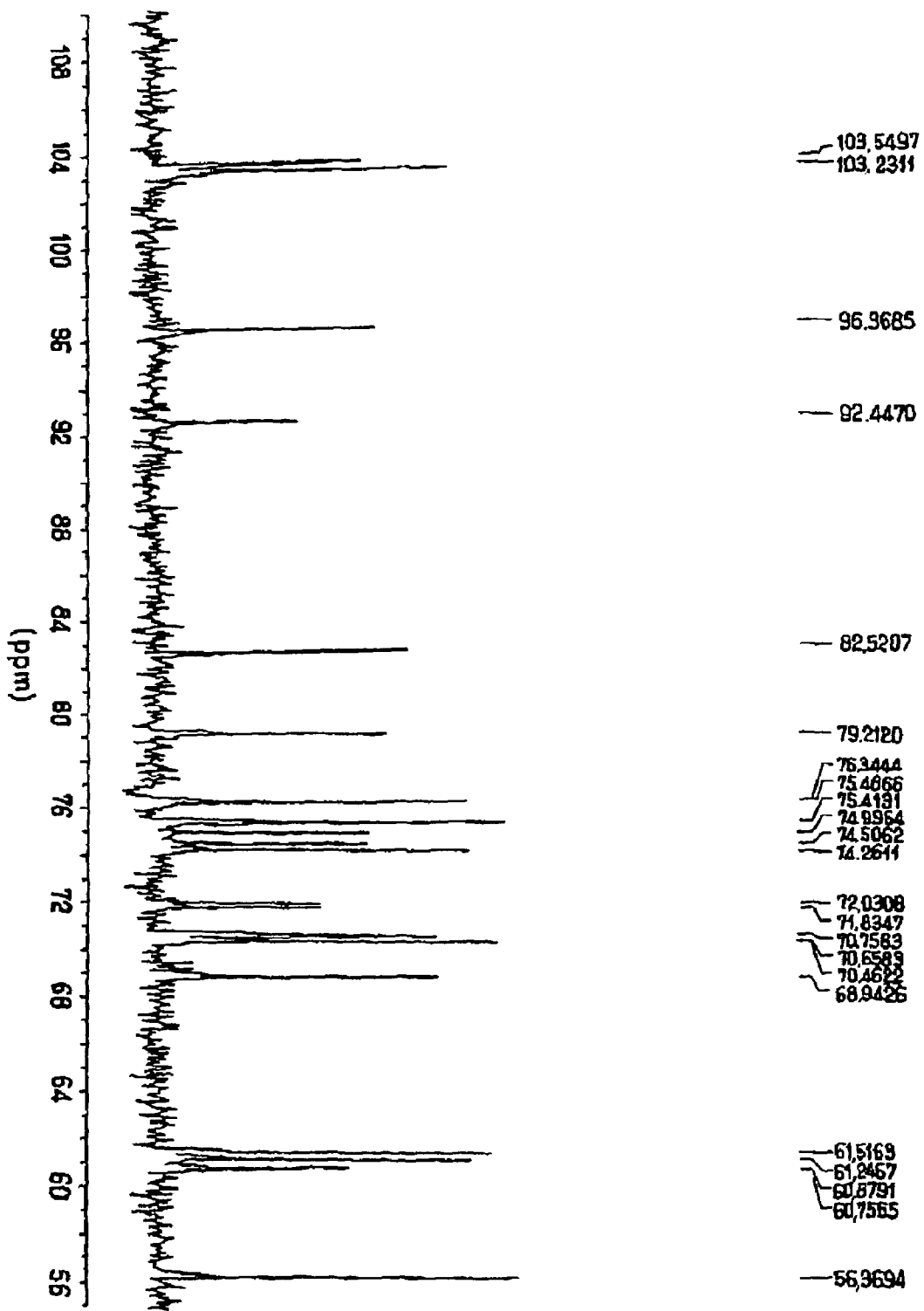

FIG. 5: ¹³C NMR spectrum of the trisaccharide 4-O-[3-O-(2-acetamido-2-deoxy-β-D-glucopyranosyl)-β-D-galacto-pyranosyl]-D-glucopyranose, (β-D-GlcNAc-[1→3]-β-D-Gal-[1→4]-D-Glc)

Figure 6:
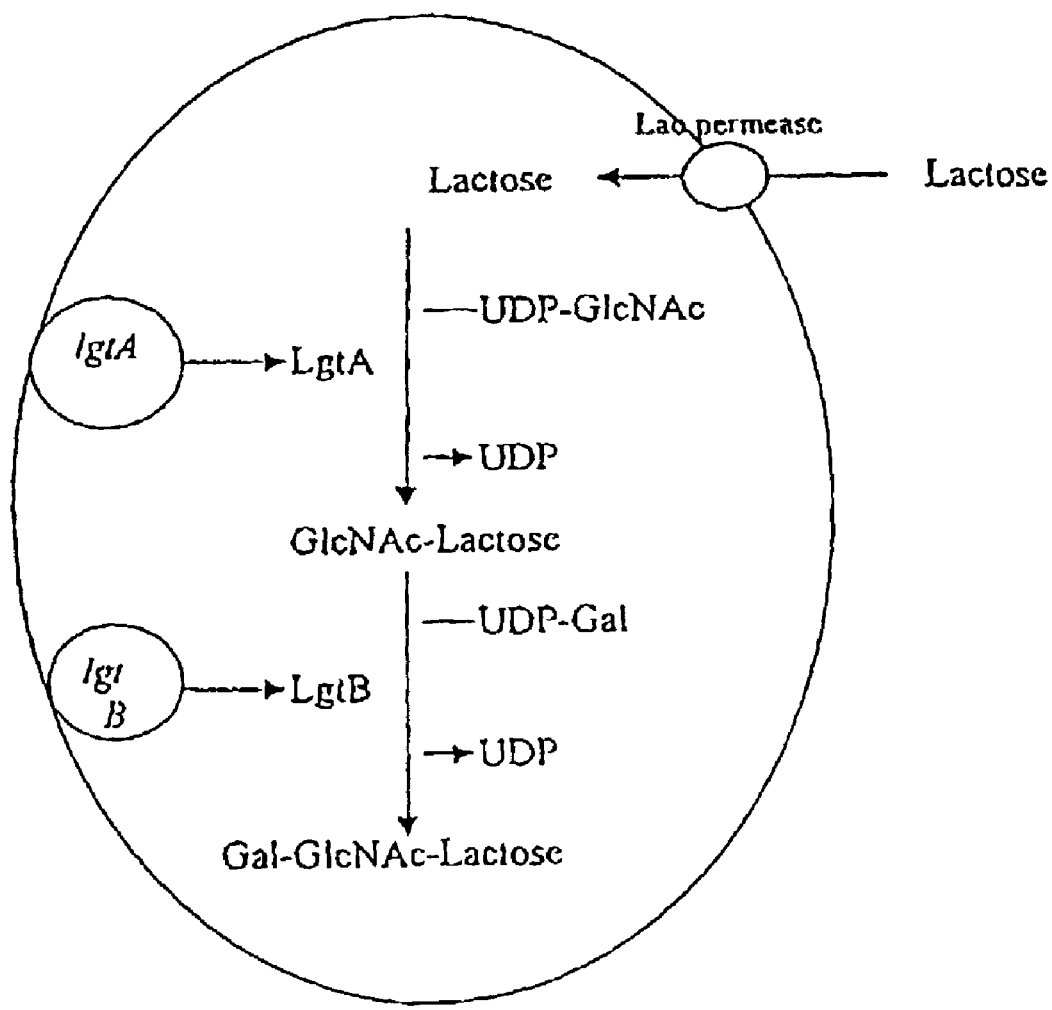

FIG. 6: Principle of the method for producing lacto-N-neo-tetraose (β-D-Gal-[1-4]-β-D-GlcNAc-[1-3]-β-D-Gal-[1-4]-β-D-Glc)

Lactose (β-D-Gal-[1-4]-β-D-Glc) is transported into the cell by Lac permease. The lactose cannot be hydrolyzed in the cell since the strain is a LacZ⁻ mutant. Expression of the lgtA gene allows the production of the LgtA enzyme which transfers a GlcNAc from UDP-GlcNAc onto a lactose molecule. The trisaccharide formed is then used as a precursor by LgtB which transfers a galactose molecule from UDP-Gal to form lacto-N-neo-tetraose (β-D-Gal-[1-4]-β-D-GlcNAc-[1-3]-β-D-Gal-[1-4]-β-D-Glc).

Figure 7:
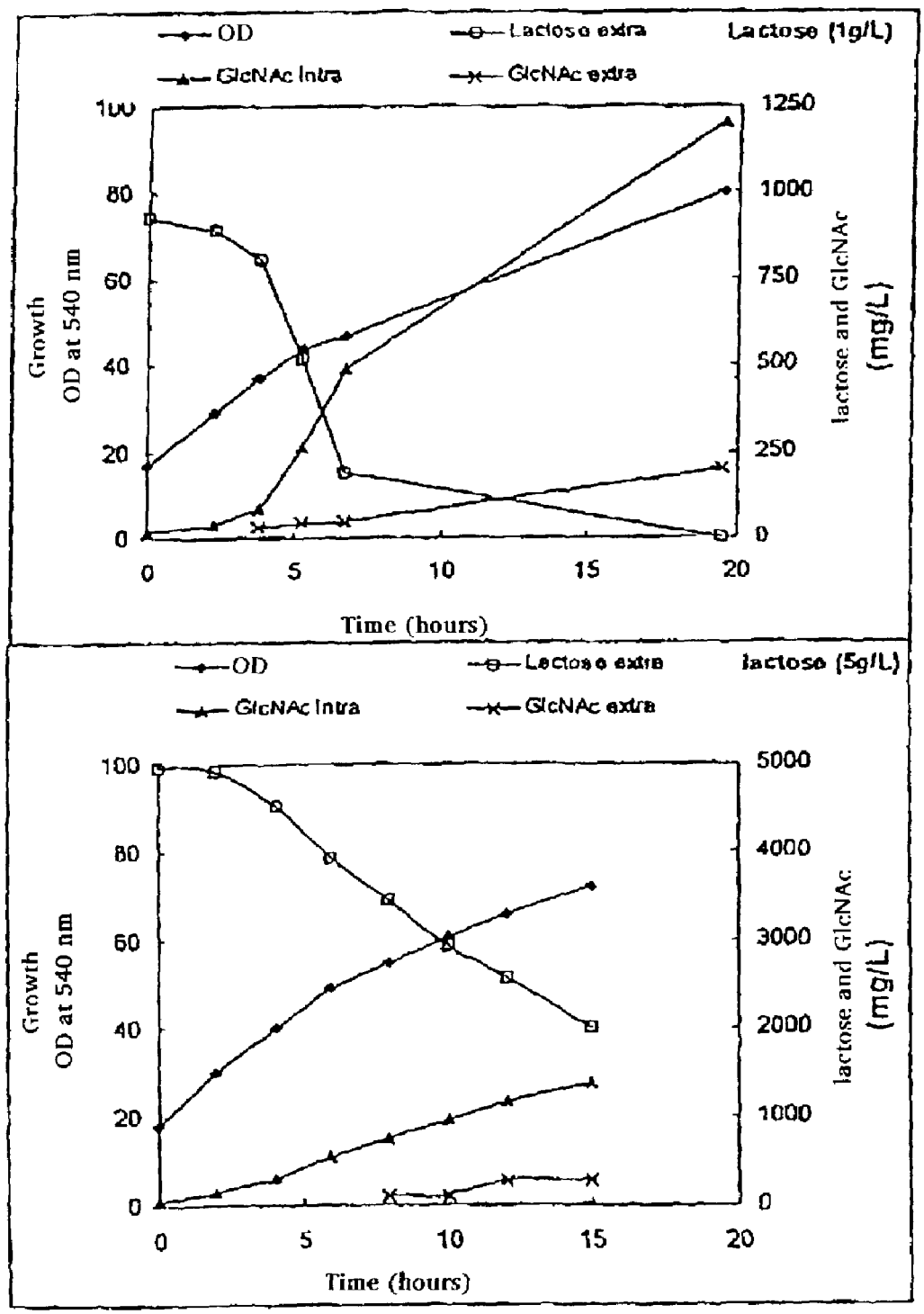

FIG. 7: High cell density culturing of the strain JM 109 (pCWlgtA, pBBlgtB)

Culturing in the presence of lactose at high concentration (5 g.l⁻¹) and at low concentration (1 g.l⁻¹).

Figure 8:
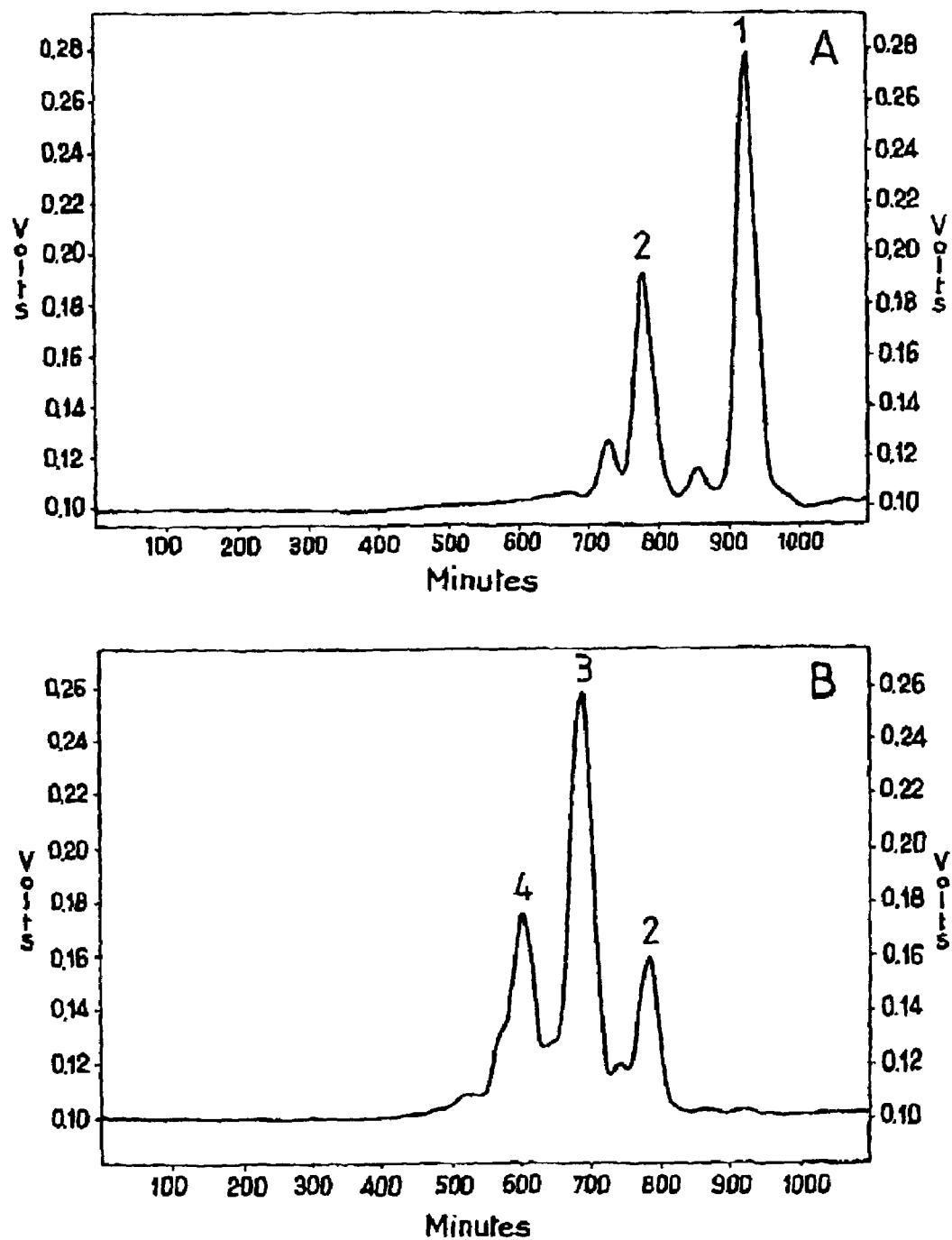

FIG. 8: Separation on Biogel P4 of the oligosaccharides produced by the strain JM 109 (pCWlgtA, pBBlgtB) in the presence of lactose at an initial concentration of 5 g.l⁻¹ (A) or of 1 g.l⁻¹ (B)

The peaks 1, 2, 3 and 4 correspond, respectively, to lacto-N-neo-tetraose, lacto-N-neo-hexaose, lacto-N-neo-octaose and lacto-N-neo-decaose.

Figure 9:
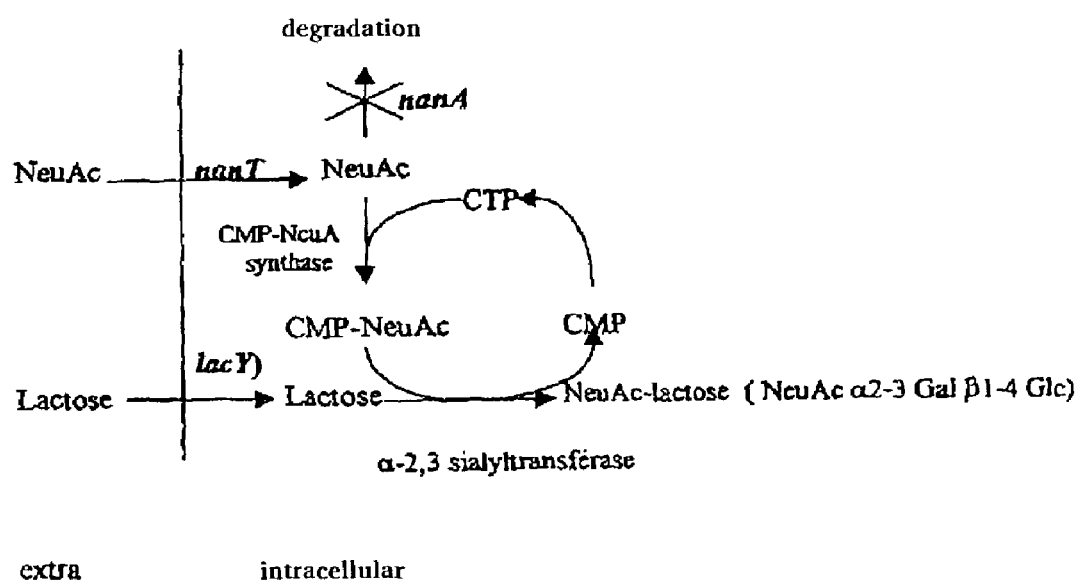

FIG. 9: Principle of the method for producing sialyllactose

Lactose and sialic acid (NeuAc) are internalized in the cell by lactose permease (lacy) and sialic acid permease (nanT). These two compounds are not degraded in the cell since the strain is a lacZ⁻ and nanA⁻ mutant. The expression of CMP-NeuA synthase and of α-2,3-sialyl-transferase allows the activation of the sialic acid internalized into CMP-NeuAc and its transfer onto the intracellular lactose.

EXAMPLES

Example 1

Materials and Methods 1.1. Origin of the Plasmids and Bacterial Strains

The strains JM 107 and JM 109 of *Escherichia coli* K12 (Yannisch-Perron et al., 1984) were used as host cells for all the oligosaccharide production examples described. The strains were obtained from the DSM (Deutsche Sammlung von Mikroorganismen). The genotype of the strain JM 109 is as follows: F traD36 lacI$^q$ Δ(lacZ)M15 proA⁺B⁺/e14⁻ (McrA⁻) Δ(lac-proAB) supE44 recA1 endA1 gyrA96 (Nal$^r$) thi hsdR17 relA1. The genotype of the strain JM 107 is identical to that of the strain JM 109 except for the fact that the recA1 gene is not inactivated.

The lgtA and lgtB genes of *Neisseria meningitis* MC58 were supplied by Dr W. Wakarchuk (Institute for Biological Sciences, National Research Council of Canada, 100 Sussex Drive, Ottawa, Ontario, K1A OR6, Canada) in the form of two plasmids pCW, one containing the lgtA gene (referred to herein as pCWlgtA) and the other containing the lgtB gene (referred to herein as pCWlgtB). The sequences of these two genes are available from the GenBank databank under the number U25839. The plasmid pLitmus28 was purchased from the company New Englands Biolabs. The plasmid pBBR1MCS was supplied by Dr M. Kovach (Department of Microbiology and Immunology, Louisiana State University, Shreveport, La. 71130-3932, USA).

The genes for CMP-sialic acid synthase and α-2,3-sialyl-transferase of *Neisseria meningitis* MC58 were supplied by Dr M. Gilbert (Institute for Biological Sciences, National Research Council of Canada, '100 Sussex Drive, Ottawa, Ontario, K1A OR6, Canada) in the form of two plasmids NSY-01 and NST-01. The plasmid NSY-01 is a derivative of the plasmid pT7-7 which contains the gene (GenBank U60146) for CMP-sialic acid synthase (Gilbert et al., 1997). The plasmid NST-01 is a derivative of the plasmid pBluescript Sk⁻ which contains the gene (GenBank No. U60660) for α-2,3-sialyl-transferase (Gilbert et al., 1996).

The gene fucT for α-1,3-fucosyl-transferase of *Helicobacter pylori* was supplied by Dr S. Martin (Glaxo Wellcome Research and Development, Gunnels Wood Road, Stevenage, Hertfordshire, SG1 2NY, UK) in the form of a plasmid pHP0651 derived from pET-21a. The sequence is available from the GenBank (AE000578, gene HPO651).

1.2. Subclonings

We used the standard techniques of molecular biology described by Sambrook et al. (1989).

construction of the plasmid pBBlgtB: the 0.835-kb DNA fragment containing the lgtB gene was obtained by digestion of the plasmid pCWlgtB with BamHI and HindIII. This fragment was subcloned into the vector pLitmus28 predigested with BamHI and HindIII to form the plasmid pLitlgtB. The 0.9-kb fragment containing the lgtB gene was excised from the plasmid pLitlgtB by digestion with XhoI and HindIII and subcloned into the plasmid pBBR1MCS predigested with XhoI and HindIII to form the plasmid pBBlgtB.

construction of the plasmid pBBnsy: The fragment containing the gene for CMP-sialic acid synthase was excised from the plasmid NSY-01 by digestion with XbaI 10 and subcloned into the plasmid pBBR1MCS predigested with XbaI to form the plasmid pBBnsy.

construction of the plasmid pBBLnt: the lgtA gene present in the construct pCWlgtA (Gilbert et al.) was amplified by PCR at the same time as the UV5 tactac promoter of the plasmid using the primers CTTTAAGCTTCCGGCTCG-TATAA (SEQ ID NO: 1) (sense, upstream promoter) and GACAGCTTATCATCGATAAGCTT (SEQ ID NO: 2) (antisense, lgtA end) both containing a HindIII site. The 1.3-kb amplified fragment was then subcloned into the HindIII site of the vector pBBlgtB.

construction of the plasmid pBBLntRcsA: The rcsA gene (Stout et al., 1991) was first amplified by PCR starting with genomic DNA from JM 109 with the primers AGGGTAC-CCATGTTGTTCCGTTTAG (SEQ ID NO: 3) (KpnI site, rcsA left) and AATCTAGAGTAATCTTATTCAGCCTG (SEQ ID NO: 4) (XbaI site, rcsA right), and then cloned into the KnpI-XbaI sites of the vector pBBR1-MCS. The vector pBBR1-MCS-rcsA was then opened upstream of the gene by digestion with KpnI, rendered blunt (Amersham kit), freed with XbaI and inserted into the SmaI-XbaI sites of the construct pBBLnt, allowing a cloning downstream of the lgtB-UV5tactac-lgtA assembly, placing rcsA under the control of the UV5 tactac promoter.

1.3. Culture Conditions

The routine cultures and the preparation of the inocula were performed on LB medium (Sambrook et al., 1989). The high cell density cultures were prepared in a 2-liter fermenter containing an initial volume of 1 liter of medium having the following composition: glycerol (17.5 g.l$^{-1}$) or glucose (15 g.l$^{-1}$), NH$_4$H$_2$PO$_4$ (7 g.l$^{-1}$), KH$_2$PO$_4$ (7 g.l$^{-1}$), MgSO$_4$.7H$_2$O (1 g.l$^{-1}$), thiamine HCl (4.5 mg.l$^{-1}$), solution of trace elements (7.5 ml.l$^{-1}$), citric acid (0.5 g.l$^{-1}$), KOH (2 g.l$^{-1}$). The MgSO$_4$ is autoclaved separately and the thiamine is sterilized by filtration. The solution of trace elements contains: nitrilotriacetate (70 mM, pH 6.5), ferric citrate (7.5 g.l$^{-1}$), MnCl$_2$.4H$_2$O (1.3 g.l$^{-1}$), CoCl$_2$.6H$_2$O (0.21 g.l$^{-1}$), CuCl$_2$.2H$_2$O (0.13 g.l$^{-1}$), H$_3$BO$_3$ (0.25 g.l$^{-1}$), ZnSO$_4$.7H$_2$O (1.2 g.l$^{-1}$), Na$_2$MoO$_4$.2H$_2$O (0.15 g.l$^{-1}$). The antibiotics ampicillin (50 mg.l$^{-1}$) and chloramphenicol (25 mg.l$^{-1}$) are added to ensure the presence of the various plasmids. The feed solution contains glycerol (500 g.l$^{-1}$) or glucose (400 g.l$^{-1}$), MgSO$_4$.7H$_2$O (12 g.l$^{-1}$) and the solution of trace elements (25 ml.l$^{-1}$).

The high cell density cultures are inoculated at 2%.

Throughout the culturing, the dissolved oxygen content is maintained at 20% of saturation by manually controlling the flow rate of air and by automatically adjusting, the stirring speed. The pH is automatically maintained at 6.8 by addition of aqueous ammonia (15% w/v). The temperature is maintained at 34° C. for the strain JM 109(pCWlgtA) and at 28° C. for the strain JM 109(pCWlgtA, pBBlgtB). The high-density culture strategy generally comprises three phases: a first phase of exponential growth which is ensured by the carbon-based substrate (glycerol or glucose) initially present in the medium; a second phase which starts when the growth becomes limited by the carbon source, which is then added continuously at a rate of 4.5 g.h$^{-1}$.l$^{-1}$ of glycerol or 3.6 g.h$^{-1}$.l$^{-1}$ of glucose. In a third phase, this rate is reduced by 60% to slow down the growth, so as to increase the oligosaccharide content.

1.4. Assay of the Oligosaccharides

Samples (1 ml) are taken during the culturing and are immediately centrifuged in microtubes. The supernatant is retained to assay the extracellular oligosaccharides. The bacterial pellet is resuspended in 1 ml of water and is then incubated in a water bath at 100° C. for 30 minutes to rupture the cells. After a second centrifugation, the supernatant is retained to assay the intracellular oligosaccharides.

The lactose concentration is measured using an enzymatic determination kit (Roche diagnostic). The N-acetyl-glucosamine residues present in the oligosaccharides are freed by acid hydrolysis as described previously (Samain et al., 1997) and then quantified calorimetrically by the method of Reissig et al., (1955); in the description, the term "hydrolyzable GlcNAc" means the amount of GlcNAc assayed in this way.

Assaying the lactose with and without treatment with a neuraminidase makes it possible to estimate the sialyl-lactose concentration.

The total fucose is measured calorimetrically by the cysteine hydrochloride method of Dische and Shettles (1948).

1.5. Purification of the Oligosaccharides

At the end of the culturing, the bacterial cells are harvested by centrifugation. The supernatant is retained for purification of the extracellular oligosaccharides. The bacterial cells are resuspended in 1 liter of water and are then permeabilized by means of a heat treatment (30 minutes at 100° C.) to release the intracellular oligosaccharides. After a second centrifugation, these oligosaccharides are recovered in the supernatant.

The first and the second supernatant containing the extracellular and intracellular oligosaccharides, respectively, are adsorbed onto active charcoal (100 g per liter of supernatant). After rinsing with distilled water, the oligosaccharides are diluted with 50% (v/v) ethanol, concentrated by evaporation and freeze-dried.

The oligosaccharides are separated out by steric exclusion chromatography on a column (4.5 cm×95 cm) of Biogel P4, allowing the injection of about 300 mg of oligosaccharide mixture. The elution is performed with distilled water, at a flow rate of 40 ml.h$^{-1}$.

The nonfucosyl oligosaccharides are separated out by steric exclusion chromatography on a column (4.5 cm×95 cm) of Biogel P4, allowing the injection of about 300 mg of oligosaccharide mixture. The elution is performed with distilled water at a flow rate of 40 ml.h$^{-1}$.

The fucosyl oligosaccharides are separated out by steric exclusion chromatography on a column (1.5 cm×200 cm) of Biogel P2 thermostatically maintained at 60° C., allowing the injection of about 30 mg of oligosaccharide mixture. The elution is performed with distilled water at a flow rate of 30 ml.h$^{-1}$.

The sialyllactose is separated from the neutral oligosaccharides by binding onto a Dowex 1X4-400 resin (in HCO$_3^-$ form), and eluted with a gradient of NaHCO$_3$ (0 to 100 mM). The bicarbonate is then removed by treating the eluate with a Dowex 50X4-400 resin in in H$^+$ form.

1.6. Preparation of the Allyl β-D-Glucosides

Allyl β-D-galactopyranoside and allyl-N-acetyl-β-D-glucosaminide were synthesized according to the protocol described by Lee and Lee (1974).

1.7. Identification and Structural Characterization of the Oligosaccharides

The mass spectra were acquired using a mass spectrometer (Nermag R-1010C). For each experiment, the initial matrix volume is 4 μl. The products were analyzed in FAB$^+$ mode.

The NMR spectra were obtained using a Brucker AC300 spectrometer.

1.8. Construction of the Strain JM 107-nanA-

A JM 107 strain incapable of metabolizing sialic acid was prepared by insertional inactivation of the nana gene (Nan operon) encoding NeuAc aldolase (Plumbridge et al., 1999). Two PCR amplification reactions were performed on either side of the center of the nanA gene so as to insert therein a BamHI restriction site.

A first 1.6-kb BamHI-XbaI fragment comprising the right-hand portion of nanA was amplified from the genomic DNA of JM 109 using the primers AAAGGATCCAAGATCAG-GATGTTCACG (SEQ ID NO: 5) and GCTCTAGAATGG-TAATGATGAGGCAC (SEQ ID NO: 6) and cloned between the BamHI and XbaI sites of the vector pUC19, forming the vector pUC-nan1.6. A second 2.1-kb KpnI-BamHI fragment comprising the left-hand portion of nanA was amplified using the primers AAAGGATCCGCGTAGGTGCGCTGAAAC (SEQ ID NO: 7) and AAAGGTACCTCAGGCCACCGT-TAGCAG (SEQ ID NO: 8) and cloned between the KpnI and BamHI sites of the vector pUC-nan1.6, forming the vector pUC-nan3.7. The kanamycin-resistance gene (pUC-4K, Pharmacia cassette) was then cloned into the BamHI site of pUC-nan3.7. The 4.9-kb SacI-XbaI fragment containing nana::kan was inserted into the same sites of the suicide vector pCVD442 (Donnenberg and Kaper, 1991). This plasmid was used to obtain by homologous recombination JM 107 nanA::kan mutants, selected for their resistance to kanamycin and their inability to metabolize sialic acid (strain JM 107-nanA$^-$).

1.9. Construction of the Strain JM 107col$^-$DE3

Suppression of the capacity to synthesize colanic acid was achieved by insertional inactivation of the wcaJ gene encoding a glucosyl-transferase (Stevenson et al., 1996). A 1.8-kb DNA fragment containing the wcaJ gene and adjacent DNA were amplified by PCR starting with genomic DNA from JM 109, and inserted into a vector pTOPO2.1 (Invitrogen PCR cloning kit), with the aid of the primers CCACGATC-CACGTCTCTCC (SEQ ID NO: 9) (right wcaJ) and AAGCT-CATATCAATATGCCGCT (SEQ ID NO: 10) (left wcaJ). It was then transferred into a pUC19 vector into the EcoRI site. The vector thus obtained was subjected to a treatment with an EcoRI methylase, allowing the subsequent addition of the kanamycin-resistance gene to the ApoI site present at the center of wcaJ. The recombinant DNA wcaJ::kan was finally transferred into the suicide vector pCVD442 allowing, by homologous recombination, the production of JM 107 genomic mutants containing the inactivated gene, selected by PCR with the aid of the primers which were used for the cloning (strain JM 107-col$^-$).

1.9. Construction of the Strain JM 107col$^-$DE3

Suppression of the capacity to synthesize colanic acid was achieved by insertional inactivation of the wcaJ gene encoding a glucosyl-transferase (Stevenson et al., 1996). A 1.8-kb DNA fragment containing the wcaJ gene and adjacent DNA were amplified by PCR starting with genomic DNA from JM 109, and inserted into a vector pTOPO$_{2.1}$ (Invitrogen PCR cloning kit), with the aid of the primers CCACGATC-CACGTCTCTCC (right wcaJ) and AAGCTCATAT-CAATATGCCGCT (left wcaJ). It was then transferred into a pUC19 vector into the EcoRI site. The vector thus obtained was subjected to a treatment with an EcoRI methylase, allowing the subsequent addition of the kanamycin-resistance gene to the ApoI site present at the center of wcaJ. The recombinant DNA wcaJ::kan was finally transferred into the suicide vector pCVD442 allowing, by homologous recombination, the production of JM 107 genomic mutants containing the inactivated gene, selected by PCR with the aid of the primers which were used for the cloning (strain JM 107-col$^-$).

The strain JM 107-col$^-$ was made lysogenic for the phage λDE3 using the lysogenization kit from Novagen.

Example 2

Production of the trisaccharide 4-O-[3-O-(2-acetamido-2-deoxy-β-D-glucopyranosyl)-β-D-galactopyranosyl]-D-glucopyranose, (A-D-GlcNAc-[1→3]-β-D-Gal-[1→4]-D-Glc)

The principle is illustrated by FIG. 1. We used the strain JM 109 of *Escherichia coli* K12, into which we introduced the plasmid pCWlgtA lgtA gene. The strain JM 109 is lacZ$^-$, that is to say that it is incapable of hydrolyzing lactose. On the other hand, it is lacY$^+$, which means that it can synthesize lactose permease. The lgtA gene encodes a β-1,3-N-acetyl-glucosaminyl-transferase (LgtA), which transfers an N-acetyl-glucosamine unit onto the galactose of lactose.

The strain JM 109 (pCWlgtA) and also the JM 109 control strain were cultured at high cell density (Samain et al., 1997) on glycerol as the carbon and energy sources. After the first phase of exponential growth provided by the glycerol initially present in the medium (17.5 g/l), the growth becomes limited by the glycerol, which is then added continuously at a rate of 4.5 g.h$^{-1}$.l$^{-1}$. During this second culturing phase, 90 mg.h$^{-1}$.l$^{-1}$ of lactose are introduced continuously. IPTG (isopropyl-β-D-thiogalactoside) (0.5 μM) is also injected at the start of this phase to induce the expression of the lactose permease and of the β-1,3-N-acetyl-glucosaminyl-transferase. As described in FIG. 2, the added lactose is virtually not accumulated in the medium, indicating that the lactose is indeed internalized by the bacterial cells. A large accumulation in the culture medium of a compound containing N-acetylglucosamine (hydrolyzable GlcNAc) is observed with the strain JM 109 (pCWlgtA). The amount of hydrolyzable GlcNAc (3.8 mmol/l) produced corresponds almost stoichiometrically to the amount of lactose consumed (3.5 mmol/l), suggesting that all of the lactose internalized has been glycosylated by LgtA.

At the end of the culturing, the cells are removed by centrifugation and the oligosaccharides present in the supernatant are purified by adsorption onto active charcoal and elution with ethanol. The oligosaccharides present are then separated out according to their molecular weight, on a Biogel P4 column. A single predominant compound is found. The mass spectrometry and NMR data indicate that this compound is indeed the trisaccharide (β-D-GlcNAc-[1→3]-β-D-Gal-[1→4]-β-D-Glc) formed by the addition of a GlcNAc residue to a lactose molecule. Indeed, the mass spectrum in FAB$^+$ mode shows the presence of a quasi-molecular ion [M+H]$^+$ at m/z 546 (FIG. 3). The $^1$H NMR spectrum confirms the trisaccharide structure, the presence of an acetyl group and the β configuration of the two O-glycoside linkages (FIG. 4). The $^{13}$C NMR spectrum also specifies that the linkage between the GlcNAc and the galactose is indeed of 1,3 type (FIG. 5).

Example 3

Production of lacto-N-neo-tetraose and of Polylactosamine

The principle is described in FIG. 6. The strain of *E. coli* JM 109 was cotransformed with the two plasmids pCWlgtA and pBBlgtB bearing, respectively, the genes lgtA (used previously) and lgtB (encoding a β-1,4-galactosyl-transferase known as LgtB). The strain JM 109 (pCWlgtA, pBBlgtB) was cultured at high cell density using glucose as the growth substrate. At the start of the second phase, lactose is added at high concentration (5 g.l$^{-1}$) or at low concentration (1 g.l$^{-1}$)

and 0.1 mM IPTG is added. Contrary to what was observed with the strain JM 109 (pCWlgtA), only a weak release of hydrolyzable GlcNAc into the medium is detected during the culturing of this strain. On the other hand, hydrolyzable GlcNAc is found in large amount in the bacterium (FIG. 7). When the supply of lactose is 1 g.l$^{-1}$, complete internalization of the lactose (2.9 mmol.l$^{-1}$) and a total production of bound GlcNAc of 1.45 g.l$^{-1}$ (6.5 mmol.l$^{-1}$), i.e. the incorporation of more than 2 GlcNAc molecules per acceptor lactose molecule, are observed. When the lactose is added in high concentration, the internalization is incomplete (3 g.l$^{-1}$, i.e. 8.7 mmol.l$^{-1}$) with a production of GlcNAc also of about 6.5 mmol.l$^{-1}$. In this case, the GlcNAc/lactose molar ratio is close to 1, which is coherent with the synthesis of lacto-N-neo-tetraose.

The purification of the intracellular oligosaccharide fraction made it possible to obtain several main compounds that are well separated by chromatography on Biogel P4. The mass spectrometry and NMR data indicate that these compounds correspond to the following structures: lacto-N-neo-tetraose [M+H]$^+$=708; lacto-N-neo-hexaose [M+H]$^+$=708; lacto-N-neo-octaose [M+Na]$^+$=1460 and probably lacto-N-neo-decaose. The respective proportions of these various compounds depend on the amount of lactose added. Thus, with 5 g.l$^{-1}$ of lactose, the major product is lacto-N-neo-tetraose (FIG. 8A). On the other hand, a lower supply of lactose (1 g.l$^{-1}$) promotes the formation of compounds with a higher degree of polymerization, lacto-N-neo-octaose becoming the major product (FIG. 8B).

The formation of higher polylactosamine homologs of lacto-N-neo-tetraose is explained by the fact that LgtA is capable of using lacto-N-neo-tetraose to form an intermediate pentasaccharide that is glycosylated by LgtB to give lacto-N-neo-hexaose. The latter compound is itself the precursor for a new glycosylation cycle resulting in the formation of lacto-N-neo-octaose, and so on upto lacto-N-neo-decaose.

No significant formation of oligosaccharides with an odd number of residues and bearing a galactose in a nonreducing end position is observed. This indicates that the elongation of the molecules is limited by the incorporation of GlcNAc by LgtA rather than by the galactosylation catalyzed by LgtB.

Example 4

Production of allyl 3-O-(2-acetamido-2-deoxy-β-D-glucopyranosyl)-β-D-galactopyranoside, (β-D-GlcNAc-[1→3]-β-D-Gal-1→O-allyl)

The strain JM 109(pCWlgtA) was cultured at high cell density on glycerol. At the start of the second phase of culturing, 0.75 g.l$^{-1}$ of allyl-β-D-galactopyranoside and 0.1 mM of IPTG are added. A total internalization of the allyl-β-D-galactopyranoside is observed after 9 hours, with a stoichiometric appearance of hydrolyzable GlcNAc in the extracellular medium. The oligosaccharides present in the extracellular medium are purified as in Example 2. The mass spectrum in FAB+mode of the major product obtained shows the presence of a quasi-molecular ion [M+H]$^+$ at m/z 424 corresponding to the structure β-D-GlcNAc-[1→3]-β-D-Gal-A→O-allyl.

Example 5

Production of β-D-Gal-[1→4]-β-D-GlcNAc-1→O-allyl

The strain JM 109 (pBBlgtB) was cultured at high cell density on glycerol. At the start of the second phase of culturing, 0.5 g.l$^{-1}$ of allyl-N-acetyl-β-D-glucosaminide (β-D-GlcNAc-1→O-allyl) is added. An approximately 30% reduction in the amount of extracellular hydrolyzable GlcNAc is observed in the first five hours, which demonstrates a partial internalization of allyl-N-acetyl-β-D-glucosaminide. In parallel, an almost stoichiometric intracellular production of hydrolyzable GlcNAc and of β-linked galactose residues (hydrolyzable with β-galactosidase) is observed. These results demonstrate that 30% of the allyl-N-acetyl-β-D-glucosaminide initially added has been galactosylated by the activity encoded by the lgtB gene. After purification, the structure of the expected compound (β-D-Gal-[1→4]-β-D-GlcNAc-1→O-allyl) was confirmed by mass spectrometry and NMR.

Example 6

Production of Analogs of lacto-N-neo-tetraose and of Polylactosamines in Which the Glucose Residue is Replaced with an Allyl Group The strain JM 109 (pCWlgtA and pBBlgtB) was cultured as in Example 3, except that the supply of lactose was replaced with the addition of 0.65 g.l$^{-1}$ of allyl-β-D-galactopyranoside. After purification according to the protocol of Example 3, three main compounds are obtained. The mass spectrometry data indicate that these three compounds correspond to the tri-, penta- and heptasaccharides below:

β-D-Gal-[1→4]-β-D-GlcNAc-[1→3]-β-D-Gal-1→O-allyl, [M+H]=586;

β-D-Gal-[1→4]-β-D-GlcNAc-[1→3]-β-D-Gal-[1→4]-D-GlcNAc-[1→3]-β-D-Gal-1→O-allyl, [M+H]=951;

β-D-Gal-[1→4]-β-D-GlcNAc-[1→3]-β-D-Gal-[1→4]-β-D-GlcNAc-[1→3]-β-D-Gal-[1→4]-β-D-GlcNAc-[1→3]-β-D-Gal-1→O-allyl, [M+H]=1316.

Example 7

Production of 3'-sialyllactose (α-NeuAc-[2→3]-β-D-Gal-[1→4]-β-D-Glc)

The principle is illustrated by FIG. 9. The genes for the biosynthesis of sialic acid and CMP-NeuAc are not present in *E. coli* K12. However, *E. coli* K12 is capable of degrading sialic acid (Plumbridge and Vimr, 1999) and contains a permease (NanT) that enables exogenous sialic acid to enter into the cell. This sialic acid is then normally catabolized by an aldolase (NanA).

We used the strain of *Escherichia coli* K12 JM 107-nanA$^-$ (Example 1) and a JM 107 control strain into which we introduced the two compatible plasmids NST-01 and pBBnsy containing, respectively, the genes for α-2,3-sialyl-transferase and for CMP-NeuAc synthase. This strain lacks nanA activity and is thus incapable of degrading intracellular sialic acid. However, it contains the lactose permease (lacy) and sialyl permease (nanT) genes and is thus capable of internalizing exogenous sialic acid and lactose. The internalized sialic acid may thus be activated to CMP-NeuAc by the action of CMP-NeuAc synthase and transferred onto the intracellular lactose by the action of α-2,3-sialyl-transferase.

The strain JM 107-nanA⁻ (Nst-01, pBBnsy) and the JM 107 control strain (Nst-01, pBBnsy) having the NanA activity were cultured at high cell density on glycerol. Lactose (1.5 g.l⁻¹), IPTG (0.1 mM) and sialic acid (0.6 g.l⁻¹) are added at the start of the second phase of culturing for a period of five hours. Throughout the duration (17 hours) of the third phase of culturing, 100 mg.h⁻¹.L⁻¹ of sialic acid and 200 mg.h⁻¹L⁻¹ of lactose are introduced continuously.

At the end of culturing of the strain JM 107-nanA⁻(Nst-01, pBBnsy), enzymatic assay of the lactose with and without treatment with a neuraminidase makes it possible to estimate the total production of sialyllactose as 2.6 g.l⁻¹. This production is partly found in the bacterial cells (1.5 g.l⁻¹) and in the extracellular culture medium (1.1 g.l⁻¹). In the case of the JM 107 control strain (Nst-01, pBBnsy), the production of sialyllactose is much lower (150 mg.l⁻¹), indicating that virtually all of the sialic acid has been degraded by the bacterium.

The intracellular and extracellular oligosaccharides are purified by adsorption onto active charcoal and elution with ethanol. After purification on an anion-exchange resin, only one product is detected by HPLC.

The mass spectrum in FAB⁺ mode shows the presence of two quasi-molecular ions [M+H]+at m/z 656 and [M+Na] at m/z 678 corresponding to the sodium salt of sialyllactose.

Example 8

Production of Fucosyl Derivatives of lacto-N-neo-tetraose

In *E. coli* K12, the genes for the biosynthesis of GDP-fucose form part of the operon responsible for the biosynthesis of an extracellular polysaccharide, colanic acid (Stevenson et al., 1996). The expression of this operon is controlled by a complex regulation network in which the protein RcsA is involved (Stout et al., 1991). The overexpression of the rcsA gene is thus reflected by an overproduction of colanic acid (Russo and Singh, 1993) and consequently of the genes for the biosynthesis of GDP fucose.

To increase the availability of GDP fucose, our strategy consisted in using a strain of *E. coli* in which the rcsA gene was overexpressed (so as to overproduce the genes for the biosynthesis of GDP-fucose) and in which one of the genes that is essential to the biosynthesis of colanic acid has been inactivated (so as to totally suppress the production of colanic acid and to avoid a competition for the use of GDP-fucose).

We used the strain JM 107-col⁻DE3 in which the wcaJ gene, which is responsible for the transfer of the first glucose residue of the repeating unit, has been inactivated according to Example 1 and into which we introduced either the two plasmids pHP0651 and pBBLnt, or the two plasmids pHP0651 and pBBLntRcsA. The plasmid pHP0651 contains the fucT gene for α-1,3-fucosyl-transferase of *Helicobacter pylori*. This fucosyl-transferase uses as acceptor N-acetyllactosamine and lacto-N-neo-tetraose, but not lactose (Martin et al., 1997). The plasmid pBBLnt contains the lgtA and lgtB genes. The plasmid pBBLntRcsA contains the lgtA, lgtB and rcsA genes.

The two strains JM 107-col⁻DE3 (pHP0651, pBBLnt) and JM 107-col⁻DE3 (pHP0651, pBBLntRcsA) were cultured as in Example 3 in the presence of 5 g.l⁻¹ of lactose. At the end of the third phase of culturing, the amount of hydrolyzable GlcNAc produced by the two strains (1.7 g.l⁻¹) was comparable to that obtained with the strain JM 109 (pCWlgtA, pBBlgtB) in Example 3. The colorimetry assay of the fucose at the end of culturing shows a large difference between the two strains, with a fucose production of 1 g.l⁻¹ for the strain JM 107-col⁻DE3 (pHP0651, pBBLntRcsA) and only 0.25 g.l⁻ for the strain JM 107-col⁻DE3 (pHP0651, pBBLnt). The fucosyl oligosaccharides are found at more than 70% in the intracellular fraction.

Purification of the intracellular fraction by adsorption onto active charcoal and steric exclusion chromatography on Biogel P2 makes it possible to separate four main compounds.

Compound 1 corresponds, by its elution volume on Biogel P2 and its thin-layer migration, to lacto-N-neo-tetraose.

The mass spectrum of compound 2 shows the presence of a quasi-molecular ion [M+H]⁺at m/z 854 corresponding to the molar mass of lacto-N-fucopentaose. The presence of a secondary ion at 327 indicates that the molecule is fucosylated on the glucose residue and has the following structure β-D-Gal-[1→4]-β-D-GlcNAc-[1→3]-β-D-Gal-[1→4]-(α-L-Fuc-[1→3])-β-D-Glc.

The mass spectrum of the major compound 3 shows the presence of 3 quasi-molecular ions at m/z 1000, 1022 and 1038 corresponding to the three forms [M+H]⁺, [M+Na]+ and [M+K]+ of the lacto-N-difucohexaose molecule having the following structure β-D-Gal-[1→4]-4-(β-L-Fuc-[1→3])-β-D-GlcNAc-[1→3])-β-D-Gal-[1→4]-(α-L-Fuc-[1→3])-β-D-Glc.

The mass spectrum of compound 4 makes it possible to identify two quasi-molecular ions at m/z 1365 and 1388 corresponding to the [M+H]⁺ and [M+Na]⁺ forms of a lacto-N-difucooctaose molecule. The presence of a secondary ion at m/z 512 indicates that the GlcNAc residue of the nonreducing end bears a fucose. The NMR data show that the ¹H proton of a fucose residue is sensitive to anomerism and that this fucose residue is thus bound to the glucose. These results make it possible to propose the following structure for compound 4: β-D-Gal-[1→4]-(α-L-Fuc-[1→3])-β-D-GlcNAc-[1→3]-β-D-Gal-[1→4]-β-D-GlcNAc-[1→3]-β-D-Gal-[1→4]-(α-L-Fuc-[1→3])-β-D-Glc.

REFERENCES

1. Boons (1996) *Tetrahedron* 52, 1095-1121.
2. Dische Z., Shettles L. B. (1948) *J. Biol. Chem.*, 175, 160-167.
3. Donnenberg M. S., Kaper J. B. (1991) *Infect. Immun.*, 59, 4310-4317.
4. Geremia R. A., Mergaert P., Geelen D., Van Montagu M., Holsters M. (1994) *Proc. Natl. Acad. Sci. USA*, 91, 2669-2673.
5. Gilbert M., Watson D. C., Cunningham A. M., Jennings M. P., Young N. M., Martin A., Wakarchuk W. W. (1996) *J. Biol. Chem.*, 271, 28271-28276.
6. Gilbert M., Watson D. C., Wakarchuk W. W. (1997) *Biotechnology Letters*, 19, 417-420.J.
7. Gilbert M., Cunningham A. M., Watson D. C., Martin A., Richards J. C., Wakarchuk W. W. (1997) *Eur. J. Biochem.* 249, 187-194.
8. Kamst E., van der Drift K. M. G., Thomas-Oates J. E., Lugtenberg B. J. J., Spaink H. P. (1995) *Escherichia coli J. Bacteriol.* 177, 6282-6285.
9. Kovach M. E., Elzre P. H., Hill D. S., Roberts on G. T., Rarris M. A., Roop II, R. M., Peterson K. M. (1995) *Gene* 166, 175-176.
10. Lee R. T., Lee Y. C. (1974) *Carbohyd. Res.* 37, 193-203.
11. Martin S. L., Edbrooke M. R., Hodgman T. C., van den Eijnden D. H., Bird M. I. (1997) *J. Biol. Chem.* 34, 21349-21356.

12. Mergaert P., D'Haeze W., Geelen D., Promé D., Van Montagu M., Geremia R., Promé J. C., Holsters M. (1995) *J. Biol. Chem.* 270, 29217-29223.
13. Plumbridge J., Vimr E. (1999) *J. Bacteriol.* 181, 47-54.
14. Reissig J. L., Strominger J. L., Leloir L. F. (1955) *J. Biol. Chem.* 217, 959-966.
15. Roy R. (1997) Recent developments in the rational design of multivalent glycoconjugates, in *Topics Curr. Chem.*, (eds J. Thiem and H. Driguez), Springer, Heidelberg, pp. 241-274.
16. Russo T. A., Singh G. (1993) *J. Bacteriol.* 175, 7617-7623.
17. Samain E., Drouillard S., Heyraud A., Driguez H., Geremia R. A. (1997) *Carbohyd. Res.* 30, 235-242.
18. Sambrook J., Fritsch E. F., Maniatis T. (1989) Molecular cloning: a laboratory manual, 2nd ed. Cold Spring Harbor laboratory Press. N. Y.
19. Spaink H. P., Wijfjes A. H. M., van der Drift K. M. G., Haverkamp J., Thomas-Oates J. E., Lugtenberg B. J. J. (1994) *Mol. Microbiol.* 13, 821-831.
20. Stevenson G., Andrianopoulos K., Hobbs M., P. R. Reeves P. R. (1996) *J. Bacteriol.* 178, 4885-4893.
21. Stout V., Torres-Cabassa A., Maurizi M. R., Gutnick D., Gottesman S. (1991) *J. Bacteriol.* 173, 1738-1747.
22. Yannisch-Perron C., Viera J., Messing J. (1985) *Gene,* 33, 103-119.

The invention claimed is:

1. A method for producing an oligosaccharide comprising lactose using a genetically modified cell starting with at least one internalized exogenous precursor consisting of lactose said method comprising:
   (i) obtaining a Lac Z$^-$Y$^+$ E. coli cell that comprises at least one recombinant gene encoding an enzyme capable of modifying said exogenous precursor or one of the intermediates in the biosynthetic pathway of said oligosaccharide from said exogenous precursor necessary for the synthesis of said oligosaccharide from said exogenous precursor, and also the components for expressing said gene in said cell; and
   (ii) culturing said cell on a carbon-based substrate in the presence of at least one said exogenous precursor, under conditions inducing the internalization according to a mechanism of active transport of said exogenous precursor by said cell and the production of said oligosaccharide by said cell,
   wherein said culturing comprises:
   (a) a first phase of exponential cell growth ensured by said carbon-based substrate,
   (b) a second phase of cell growth limited by said carbon-based substrate which is added continuously,
   wherein said precursor is added during the second phase.

2. The method as claimed in claim 1, wherein said modification is selected from the group consisting of glycosylation, sulfation, acetylation, phosphorylation, succinylation, methylation, and addition of an enolpyruvate group.

3. The method as claimed in claim 1, wherein said enzyme is an enzyme capable of performing a glycosylation, chosen from glycosyl-transferases.

4. The method as claimed in claim 3, wherein said enzyme is a glycosyl-transferase selected from the group consisting of β-1,3-N-acetyl-glucosaminyl-transferase, β-1,3-galactosyl-transferase, β-1,3-N-acetyl-galactosaminyl-transferase, β-1,3-glucuronosyl-transferase, β-1,3-N-acetyl-galactosaminyl-transferase, β-1,4-N-acetyl-galactosaminyl-transferase, β-1,4-galactosyl-transferase, α-1,3-galactosyl-transferase, α-1,4-galactosyl-transferase, α-2,3-sialyl-transferase, α-2,6-sialyl-transferase, α-2,8-sialyl-transferase, α-1,2-fucosyl-transferase, α-1,3-fucosyl-transferase and α-1,4-fucosyl-transferase.

5. The method as claimed in claim 1, wherein said carbon-based substrate is selected from the group consisting of glycerol and glucose.

6. The method as claimed in claim 1, wherein said culturing is performed under conditions allowing the production of a culture with a high cell density.

7. The method as claimed in claim 6, wherein said culturing further comprises
   (c) a third phase of slowed cell growth obtained by continuously adding to the culture an amount of said substrate that is less than the amount of substrate added in said second phase so as to increase the content of oligosaccharides produced in the high cell density culture.

8. The method as claimed in claim 7, wherein the amount of substrate added continuously to the cell culture during said third phase is at least 30% less than the amount of substrate added continuously during said second phase.

9. The method as claimed in claim 1, further comprising the addition of an inducer to said culture medium to induce the expression in said cell of said enzyme and/or of a protein involved in said transport.

10. The method as claimed in claim 9, wherein said inducer is isopropyl β-D-thiogalactoside (IPTG) and said protein is lactose permease.

11. The method as claimed in claim 1, for the production of the trisaccharide 4-O-[3-O-(2-acetamido-2-deoxy-β-D-glucopyranosyl)-β-D-galactopyranosyl]-D-glucopyranose, (β-D-GlcNac-[1→3]-β-D-Gal-[1→4]-D-Glc), wherein:
   said cell is a bacterium of LacZ$^-$, LacY$^+$ genotype;
   said enzyme is β-1,3-N-acetyl-glucosaminyl-transferase;
   said substrate is glycerol;
   said inducer is isopropyl β-D-thiogalactoside (IPTG); and
   said precursor is lactose.

12. The method as claimed in claim 1, for the production of lacto-N-neo-tetraose and polylactosamine (lacto-N-neo-hexaose, lacto-N-neo-octaose, lacto-N-neo-decaose), further comprising the addition of an inducer to said culture medium to induce the expression in said cell of said enzyme and/or of a protein involved in said transport-wherein:
   said cell is a bacterium of LacZ$^-$, LacY$^+$ genotype;
   said enzymes are β-1,3-N-acetyl-glucosaminyl-transferase and β-1,4-galactosyl-transferase;
   said inducer is isopropyl-β-D-thiogalactoside (IPTG); and
   said precursor is lactose.

13. The method as claimed in claim 1, wherein said cell is cultured on said carbon-based substrate labeled with at least one isotope or in the presence of said exogenous precursor labeled with said isotope.

14. A method for producing an oligosaccharide comprising lactose by a genetically modified cell starting with at least one internalized exogenous precursor consisting of lactose, said method comprising:
   (i) obtaining a Lac Z$^-$Y$^+$ E. coli cell comprising (a) at least one recombinant gene encoding an enzyme capable of modifying said exogenous precursor, and (b) the components for expressing said gene in said cell;
   (ii) culturing said cell on a carbon-based substrate in the presence of at least one said exogenous precursor and lactose permease, under conditions inducing the internalization according to a mechanism of active transport of said exogenous precursor by said cell and the production of said oligosaccharide by said cell,
   wherein the enzyme is a glycosyl-transferase selected from the group consisting of β-1,3-N-acetyl-glucosaminyl-transferase, β-1,3-galactosyl-transferase, β-1,3-N-acetyl-galactosaminyl-transferase, β-1,3-glucuronosyl-transferase, β-1,3-N-acetyl-galactosaminyl-transferase, β-1,4-N-acetyl-galactosaminyl-transferase, β-1,4-galactosyl-transferase, α-1,3-galactosyl-transferase, α-1,4-galactosyl-transferase, α-2,3-sialyl-transferase, α-2,6-sialyl-transferase, α-2,8-sialyl-transferase, α-1,2-fucosyl-transferase, α-1,3-fucosyl-transferase and α-1,4-fucosyl-transferase, and
   wherein said culturing comprises:
   (a) a first phase of exponential cell growth ensured by said carbon-based substrate;
   (b) a second phase of cell growth limited by said carbon-based substrate which is added continuously; and
   wherein said precursor is added during the second phase.

* * * * *

UNITED STATES PATENT AND TRADEMARK OFFICE
CERTIFICATE OF CORRECTION

| | | |
|---|---|---|
| PATENT NO. | : 7,521,212 B1 | Page 1 of 1 |
| APPLICATION NO. | : 10/019954 | |
| DATED | : April 21, 2009 | |
| INVENTOR(S) | : Samain et al. | |

It is certified that error appears in the above-identified patent and that said Letters Patent is hereby corrected as shown below:

On the Title Page:

The first or sole Notice should read --

Subject to any disclaimer, the term of this patent is extended or adusted under 35 U.S.C. 154(b) by 835 days.

Signed and Sealed this
Fifteenth Day of February, 2011

David J. Kappos
*Director of the United States Patent and Trademark Office*

SEQUENCE LISTING

```
<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctttaagctt ccggctcgta taa                                              23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gacagcttat catcgataag ctt                                              23

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agggtaccca tgttgttccg tttag                                            25

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aatctagagt aatcttattc agcctg                                           26

<210> SEQ ID NO 5
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 5
aaaggatcca agatcaggat gttcacg                                              27

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gctctagaat ggtaatgatg aggcac                                               26

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaaggatccg cgtaggtgcg ctgaaac                                              27

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaaggtacct caggccaccg ttagcag                                              27

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccacgatcca cgtctctcc                                                       19

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aagctcatat caatatgccg ct                                                   22
```